(12) United States Patent
Benner

(10) Patent No.: US 9,334,534 B1
(45) Date of Patent: May 10, 2016

(54) PROCESSES REPLACING STANDARD NUCLEOTIDES BY NON-STANDARD NUCLEOTIDES AND NON-STANDARD NUCLEOTIDES BY STANDARD NUCLEOTIDES IN DNA

(76) Inventor: Steven Albert Benner, Gainesville, FL (US)

( * ) Notice: Subject to any disclaimer, the term of this patent is extended or adjusted under 35 U.S.C. 154(b) by 0 days.

(21) Appl. No.: 12/653,613

(22) Filed: Dec. 16, 2009

(51) Int. Cl.
C12P 19/34 (2006.01)
C12Q 1/68 (2006.01)
C07H 21/04 (2006.01)

(52) U.S. Cl.
CPC ........ *C12Q 1/6869* (2013.01); *C12Q 2525/117* (2013.01)

(58) Field of Classification Search
CPC ........................ C12Q 1/6869; C12Q 2525/117
USPC ............... 536/23.1, 24, 3, 24.3; 435/6.1, 91.1
See application file for complete search history.

(56) References Cited

U.S. PATENT DOCUMENTS 5,432,272 A * 7/1995 Benner ......................... 536/25.3
6,001,983 A * 12/1999 Benner ......................... 536/23.1
6,140,496 A * 10/2000 Benner ......................... 536/27.1

OTHER PUBLICATIONS

Havemann et al. Nucleosides, Nucleotides, and Nucleic Acids 27, 261-278, 2008.*

* cited by examiner

Primary Examiner — Jezia Riley

(57) ABSTRACT

This invention concerns non-standard nucleotides that can form non-standard Watson-Crick nucleobase pairs having geometries similar to the geometries of standard nucleotide pairs, but that are joined by a non-standard hydrogen bonding schemes. Disclosed are processes that yield oligonucleotides that are semi-complementary to a standard oligonucleotide, where the region of semi-complementarity pairs one or more standard nucleotides with a non-standard nucleotide, or vice versa. Duplexes formed from two semi-complementary oligonucleotides are also inventions disclosed. The processes extending a primer annealed to an oligonucleotide template with a polymerase in the presence of a non-standard nucleoside triphosphate and a mixture of standard nucleoside triphosphates, where the non-standard triphosphate is incorporated opposite the standard triphosphate because it has available a protonated or deprotonated form, or a minor tautomeric form, that is complementary in the Watson-Crick sense to the standard nucleotide, even though in its normal form (neither protonated or deprotonated, or as its major tautomer) it is complementary in the Watson-Crick sense to a non-standard nucleobase. Also disclosed are processes that exploit an intermediary nucleoside, one whose nucleobase is partially complementary to both a standard nucleotide and a non-standard nucleotide at two of their three hydrogen bonding units. Also disclosed are intermediary nucleotides whose hydrogen bonding patterns are changed by chemical reagents. Also disclosed are the vice versa processes and process pairs where standard nucleotides are incorporated opposite non-standard nucleotides, yielding clonable products that can be sequenced to determine where non-standard nucleotides were present in the parent template oligonucleotide.

12 Claims, 13 Drawing Sheets

Figure 1:
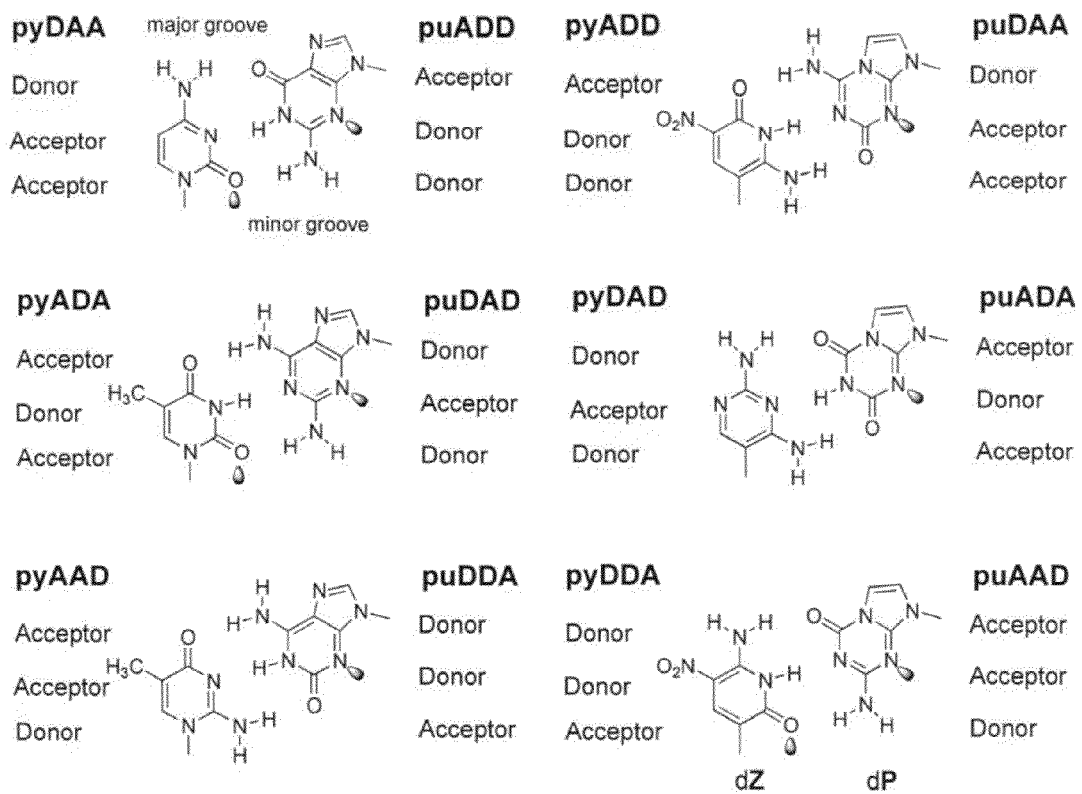

PROCESSES REPLACING STANDARD NUCLEOTIDES BY NON-STANDARD NUCLEOTIDES AND NON-STANDARD NUCLEOTIDES BY STANDARD NUCLEOTIDES IN DNA

CROSS REFERENCE TO RELATED APPLICATIONS

This application claims in part priority to the patent application filed under the PCT (with the United States as the receiving entity) having the designation US2009/003595.

STATEMENT REGARDING FEDERALLY SPONSORED RESEARCH OR DEVELOPMENT

None

NAMES OF THE PARTIES TO A JOINT RESEARCH AGREEMENT

Not applicable.

INCORPORATION-BY-REFERENCE OF MATERIAL SUBMITTED ON A DISC

None

BACKGROUND OF THE INVENTION

1. Field of the Invention

The field of this invention is nucleic acids and their analogs, more specifically nucleotide analogs that can form non-standard Watson-Crick nucleobase pairs that have similar geometry as standard Watson-Crick pairs, but are joined by a non-standard hydrogen bonding schemes. More specifically, this invention relates to processes that introduce these analogs into oligonucleotides via enzymatic processes that mismatch non-standard nucleotides against standard nucleotides to create orthogonally capturable tags. This invention further relates to processes and pairs of processes that replace non-standard nucleotides by more than one standard nucleotides, leading to clonable products and, in particular, to two clonable products whose sequences, when compared, allow the inference of the sites in the original oligonucleotide sequence where non-standard nucleotides were present.

2. Description of Related Art

Natural oligonucleotides bind to complementary oligonucleotides according to Watson and Crick rules of nucleobase pairing, where adenine (A) (or 2-aminoadenine) pairs with thymine (T) (or uracil, U), and guanine (G) pairs with cytosine (C), with complementary strands anti-parallel to one another. In this disclosure, "DNA" or "nucleic acid" is understood to include, as appropriate, both DNA (where the sugar is 2'-deoxyribose) and RNA (where the sugar is ribose), the 2'-O-alkyl and allyl derivatives, and these nucleic acids and their analogs in non-linear topologies, including dendrimers, comb-structures, and nanostructures, and these nucleic acids and their analogs carrying tags (e.g., fluorescent, functionalized, or binding) to the ends, sugars, or nucleobases, and/or non-nucleotidic material attached to the ends of the strand.

These pairing rules, which are largely context free and which can be applied without undue experimentation even by high school students, allow specific hybridization of an oligonucleotide to a complementary oligonucleotide, making oligonucleotides valuable as probes in the laboratory, in diagnostics, as messages that can direct the synthesis of specific proteins, and in other applications well known in the art. Such base pairing is used, as an example and without limitation, to capture other oligonucleotides to beads, arrays, and other solid supports, in linear and dendrimeric structures, to allow nucleic acids to fold in hairpins, beacons, and catalysts, as supports for functionality, such as fluorescence, fluorescence quenching, binding/capture tags, and catalytic functionality, as part of more complex architectures, including dendrimers and nanostructures, and as scaffolds to guide chemical reactions.

Further, nucleobase pairing is used by enzymes to catalyze the synthesis of new oligonucleotides that are complementary to template nucleotides. In this synthesis, building blocks (normally the triphosphates of ribo- or deoxyribonucleosides carrying of A, T, U, C, or G) are directed by a template oligonucleotide to form a complementary oligonucleotide with the complementary sequence. This serves as the basis for technologies for enzymatic synthesis and amplification of specific nucleic acids by enzymes such as DNA and RNA polymerase, in the polymerase chain reaction (PCR), and in a variety of architectures that may involve synthesis, ligation, cleavage, immobilization and release, inter alia, used in technology to detect nucleic acids.

The Watson-Crick pairing rules can be understood chemically as a consequence of the arrangement of hydrogen bonding groups on the heterocyclic nucleobases of the oligonucleotide, groups that can either be hydrogen bond donors or acceptors. In the standard Watson-Crick geometry, a large purine nucleobase pairs with a small pyrimidine nucleobase. Thus, the AT nucleobase pair is the same size as a GC nucleobase pair; the rungs of the DNA ladder, formed from either AT or GC nucleobase pairs, all have the same length. In this disclosure, to be "complementary in the Watson-Crick sense" means to have the Watson-Crick geometry, a full pairing (not wobble pairing) of a large purine and a small pyrimidine held together by three hydrogen bonds, or (if context demands) two hydrogen bonds, where in pairing is said to be "against" the nucleotide in the complementary strand, in an antiparallel orientation, to which it is matched.

The specificity of recognition between large and small nucleobases is determined by hydrogen bonding between the nucleobases. In standard nucleobases, hydrogen bond donors are heteroatoms (nitrogen or oxygen in the natural nucleobases) bearing a hydrogen, while hydrogen bond acceptors are heteroatoms (nitrogen or oxygen in the natural nucleobases) with a lone pair of electrons. In the Watson-Crick nucleobase pairing geometry, a six membered ring (in standard nucleobases, a pyrimidine) pairs with a ring system composed of a fused five-six ring system (in standard nucleobases, a purine), with a middle hydrogen bond linking two ring atoms, and hydrogen bonds on either side joining functional groups appended to each of the rings, with donor groups paired with acceptor groups. The AT nucleobase pair uses this hydrogen bonding pattern only partly; it is completely used in the diaminoA:T base pair.

In 1990, the instant Inventor filed the first patent application (which later issued as U.S. Pat. No. 5,432,272) disclosing compositions of matter that expanded the number of nucleobases that could pair by such simple rules. He proposed eight additional nucleobases that form four additional pairs by changing the pattern of hydrogen bond donor and acceptor groups presented by a nucleobase to the nucleobase on a complementary oligonucleotide analog [U.S. Pat. Nos. 5,432, 272, 5,965,364, 6,001,983, 6,037,120, 6,140,496, 6,627,456, 6,617,106]. These disclosures showed that the geometry of the Watson-Crick nucleobase pair could accommodate as many as 12 nucleobases forming 6 mutually exclusive pairs.

Of these, four nucleobases forming two pairs are "standard", while eight nucleobases forming four pairs were termed "non-standard". Adding the non-standard nucleobases to the standard nucleobases yielded an Artificially Expanded Genetic Information System (AEGIS). It was also noted that these nucleobases analogs might be functionalized to enable a single biopolymer capable of both genetics and catalysis.

Expanded genetic alphabets have now been explored in many laboratories, and the possibility of a fully artificial genetic system has been advanced [Swi89][Pic90] [Pic91] [Voe93] [von95][Voe96][Voe96a] [Voe96b] [Kod97][Jur98] [Lut99][Jur99][Jur00], the contents of which are incorporated by reference.

To systematize the nomenclature for the hydrogen bonding patterns, the hydrogen bonding pattern implemented on a small component of a nucleobase pair are designated by the prefix "py". Following this prefix is the order, from the major groove to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major to the minor grooves, using "A" and "D". Thus, the standard nucleobases adenine and guanine implement the standard hydrogen bonding patterns puDA- and puADD respectively.

A teaching of this disclosure is that hydrogen-bonding patterns designated using this systematic nomenclature are distinct in concept from the organic molecules that are used to implement the hydrogen-bonding patterns. Thus, guanosine is a nucleoside that implements the puADD hydrogen-bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen-bonding pattern determines, in large part, the utility of the non-standard hydrogen-bonding pattern, in various applications to which it might be applied.

The additional nucleobase pairs, because of their desirable pairing properties, chemical stability, and other features known to those skilled in they art, have been useful for a variety of purposes. For example, the nucleobase pair between 2-amino-5-methyl-1-(1'-beta-D-2'-deoxyribofuranosyl)-4(1H)-pyrimidine, also known as 2'-deoxyisocytidine, disoC, or sometimes (less correctly) isoC and implementing the pyAAD hydrogen bonding pattern, and 6-amino-1,9-dihydro-9-(1'-beta-D-2'-deoxyribofuranosyl)-3H-purin-2-one, also known as 2'-deoxyisoguanosine, disoG, or sometimes (less correctly) isoG, and implementing the puDDA hydrogen bonding pattern, is incorporated into the branched DNA diagnostics tools marketed today by Bayer and its successor, Siemens. Here, the non-standard nucleobase pair supports orthogonal molecular recognition in aqueous solution, similar to nucleic acids but with a coding system that is orthogonal to the system in DNA and RNA, Thus, it allows the assembly of the branched dendrimer in the assay free from inhibition by adventitious nucleic acid, and prevents adventitious nucleic acid from capturing signaling elements form the nanostructure in the absence of the target analyte nucleic acid, creating noise. Further, adding extra letters to the genetic alphabet speeds hybridization, presumably because it decreases the number of close mismatches where DNA dwells before finding its fully matched partner. The branched DNA assay has FDA-approval and is widely used to provide personalized patient care in the clinic.

One of the advantages of incorporating non-standard nucleotides into human diagnostic assays is that binding between oligonucleotides containing these can occur without interference from natural DNA, which is often present in abundance in samples taken from human tissues. Such binding is often used to concentrate samples from complex mixtures, on arrays or at the bottoms of plastic wells. natural DNA, built from A, T, G, and C, will interfere with A:T and G:C interactions. This leads to large amounts of noise in DNA arrays, for example. Accordingly, in the branched DNA assays, non-standard nucleotides are incorporated by chemical synthesis into the portion of tags that are used to move the analyte to a spot where it can be detected and to assemble signaling dendrimers.

Pairing between non-standard nucleotides cannot be used to directly bind natural analytes, as these analytes are themselves built from A, T, G, and C. Accordingly, when non-standard nucleotides are used to achieve orthogonality in clinical diagnostic assays [Elb04a][Elb04b], they are general appended as tags to primary probes, which are built from A, T. G, and C. The primary probes are the ones that contact the analyte targeted by the diagnostic assay. This limits considerably the use of non-standard components to achieve orthogonality and high signal-to-noise ratios in biological systems. A process that creates replicates or complements of oligonucleotides that replace in a controlled fashion standard nucleotides by non-standard nucleotides would therefore have utility. If this is sequence specific, the pairing of the resulting replicate or complement through non-standard base pairs could, in an appropriate architecture, offer an element of selectivity for the analyte in addition to those selectivity elements based on other regions of the analyte (for example, the regions that bind PCR amplification primers).

Conversely, oligonucleotides containing non-standard nucleotides cannot today be introduced into standard cloning systems. No strain used for cloning, including *E. coli* strains, is known to have the cellular machinery for making the triphosphates of non-standard nucleosides and using them to replicate DNA containing non-standard nucleotides. A process that creates replicates or complements of oligonucleotides that replace in a controlled fashion non-standard nucleotides by standard nucleotides (a vice versa process) would therefore have utility. Further, such a process would most useful if it is a process pair, where the product from one process replaces the non-standard nucleotide by one standard nucleotide, and another replaces the non-standard nucleotide by a different standard nucleotide. This makes it possible to compare the sequences of the two resulting replicates or complements to ascertain where in the oligonucleotide sequence the original non-standard nucleotide(s) was (were) found.

Mismatching is known between non-standard and standard pairs such that a standard nucleotide is incorporated opposite a nonstandard nucleotide in the template. For example, Sepiol et al. [Sep76] recognized that isoG, which presents a hydrogen bond donor-donor-acceptor pattern complementary to the acceptor-acceptor-donor pattern of isoC, exists in water to about 10% as an enol tautomeric form, which can present a hydrogen bond donor-acceptor-donor hydrogen bonding pattern complementary to T (acceptor-donor-acceptor). Work in the 1990's showed that polymerases of various types would incorporate T (or U) opposite isoG in a template, presumably by pairing between T (or U) and the minor tautomeric form of isoG [Swi93]. This caused the loss of the isoG:isoC pair in (for example) PCR reactions [Joh04], a loss that was considered throughout the art to be disadvantageous, as it appeared to deprive the product from the possibility of the PCR product of having the orthogonal isoC:isoG pair.

Struggling to suppress this mispairing between T and the minor tautomeric form of isoG, the instant Inventor and Michael Sismour exploited the discovery that the minor tautomer of isoG does not pair well with 2-thio, and replaced T with 2-thioT in a polymerase incubation [Sis05]. Therefore, products derived from a six letter PCR incorporating A, G, C, 2-thioT, isoG and isoC was able to retain the isoC and isoG non-standard components after many more cycles than a six letter PCR where standard T was used instead of 2-thioT. Thus, the products were able to retain the ability to be orthogonally bound by isoG:isoC pairing after many more cycles of PCR. Further attempting to avoid mispairing and isoG:T (or U) mismatching, 7-deazaisoG was developed [Mar04].

These examples from the prior art show the extent to which those in the art view as undesirable the mismatching between standard nucleotides and non-standard nucleotides, and thereby teach away from the instant invention, which is based on an inventive step that recognizes the utility of mismatching.

BRIEF SUMMARY OF THE INVENTION

The processes of this invention use DNA polymerases that incorporate non-standard nucleotides or intermediary nucleotides opposite standard nucleotides in a parent template to produce, after one or more polymerase extension steps, product oligonucleotides that have non-standard nucleotides replacing specific standard nucleotides in the parent. Also disclosed are vice versa processes that produce product oligonucleotides that have standard nucleotides replacing specific non-standard nucleotides in the parent.

BRIEF DESCRIPTION OF THE SEVERAL VIEWS OF THE DRAWING(S)

FIG. 1. One example of an "artificially expanded genetic information system" (AEGIS). Nucleobase pairs in this system have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. The heterocycles shown are the currently preferred implementations of the indicated hydrogen bonding patterns; others are conceivable. Electron density presented to the minor groove is shown by the shaded lobes. Note that some non-standard pyrimidines do not present this density. The nucleotides implementing the pyDDA:puAAD hydrogen bonding pattern, the topic of this paper, are at the bottom right.

Figure 2:
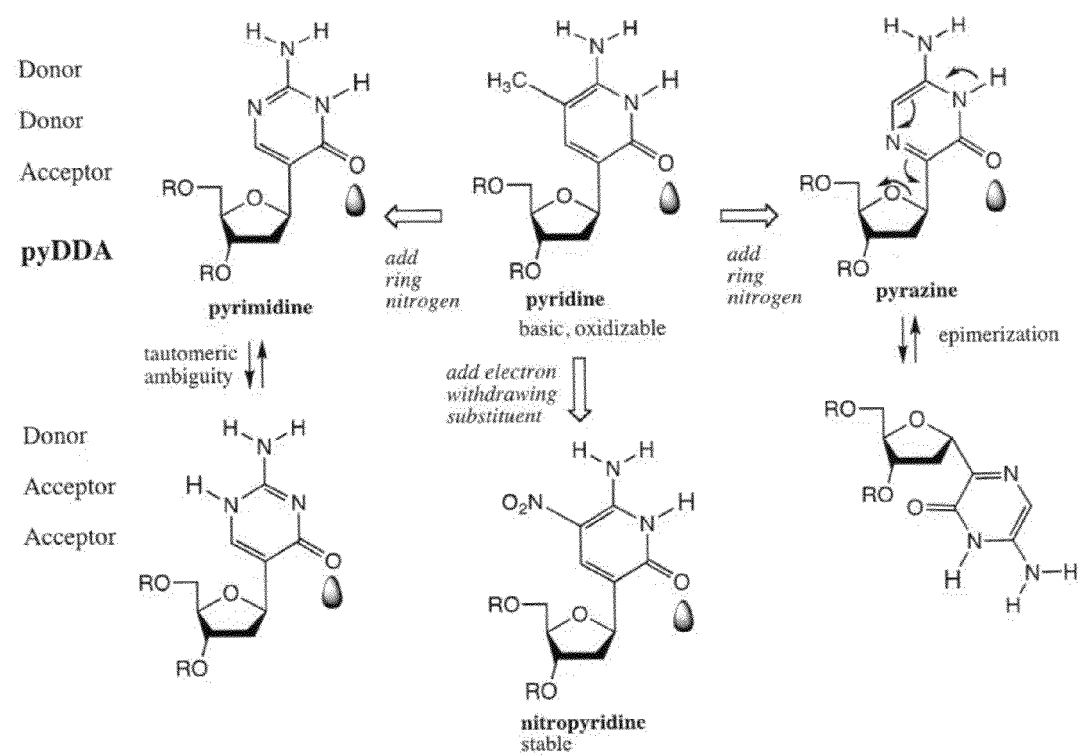

FIG. 2. Four alternative implementations of the pyDDA hydrogen bonding pattern. The implementation on a pyrimidine heterocycle suffers from tautomeric ambiguity (left). The implementation on a pyrazine suffers from facile epimerization (right). The implementation on a simple pyridine is too basic and prone to oxidation (top center). The preferred implementation is the nitropyridine heterocycle (discussed here, bottom center), which is stable to oxidation, is not basic, and does not epimerize near neutral pH.

Figure 3:
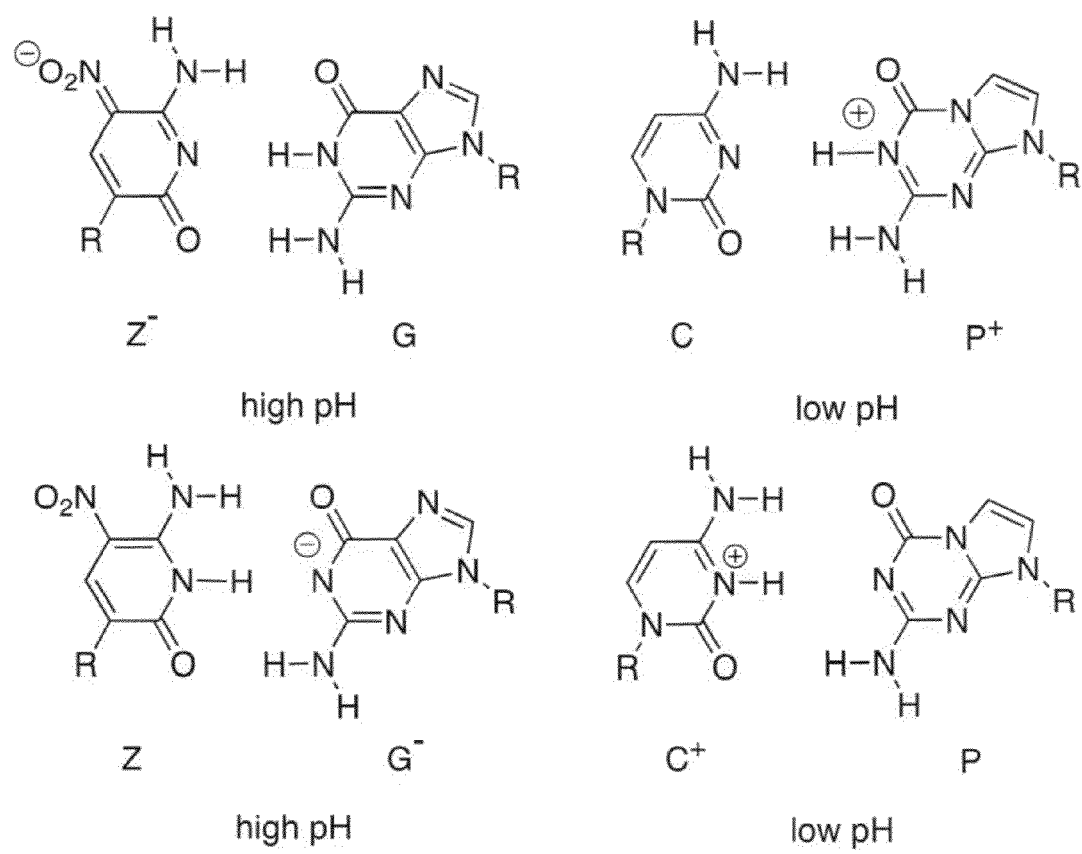
Figure 4:
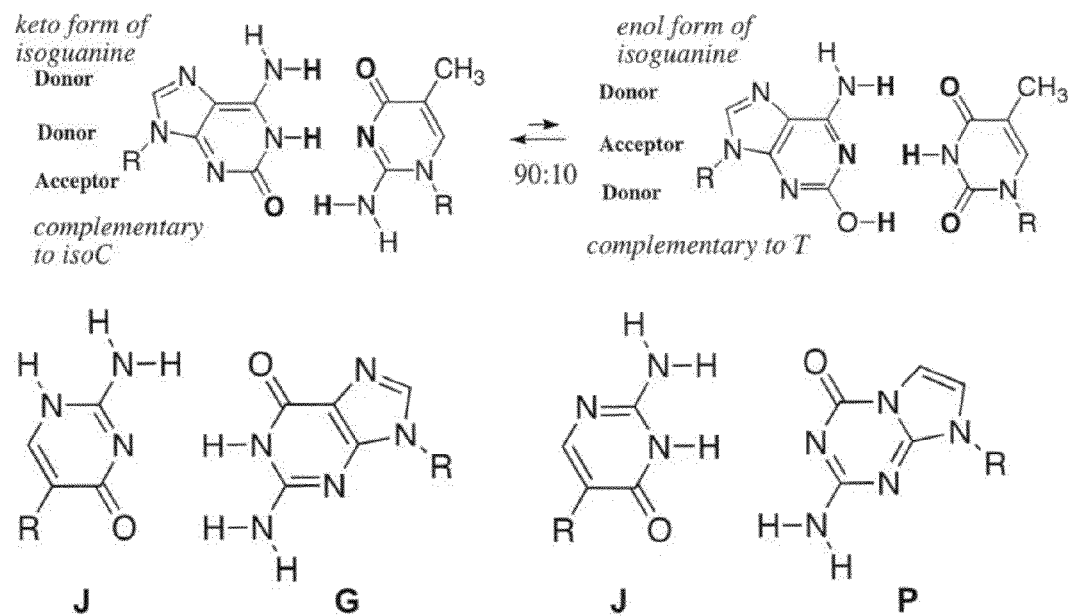

FIG. 3. Nucleobases structured to place non-standard nucleotides in a polymerase-generated product opposite specific standard nucleotides using protonated and deprotonated forms. The FIG. 4. Nucleobases structured to place non-standard nucleotides in a polymerase-generated product opposite specific standard nucleotides by virtue of their having tautomeric forms.

Figure 5:
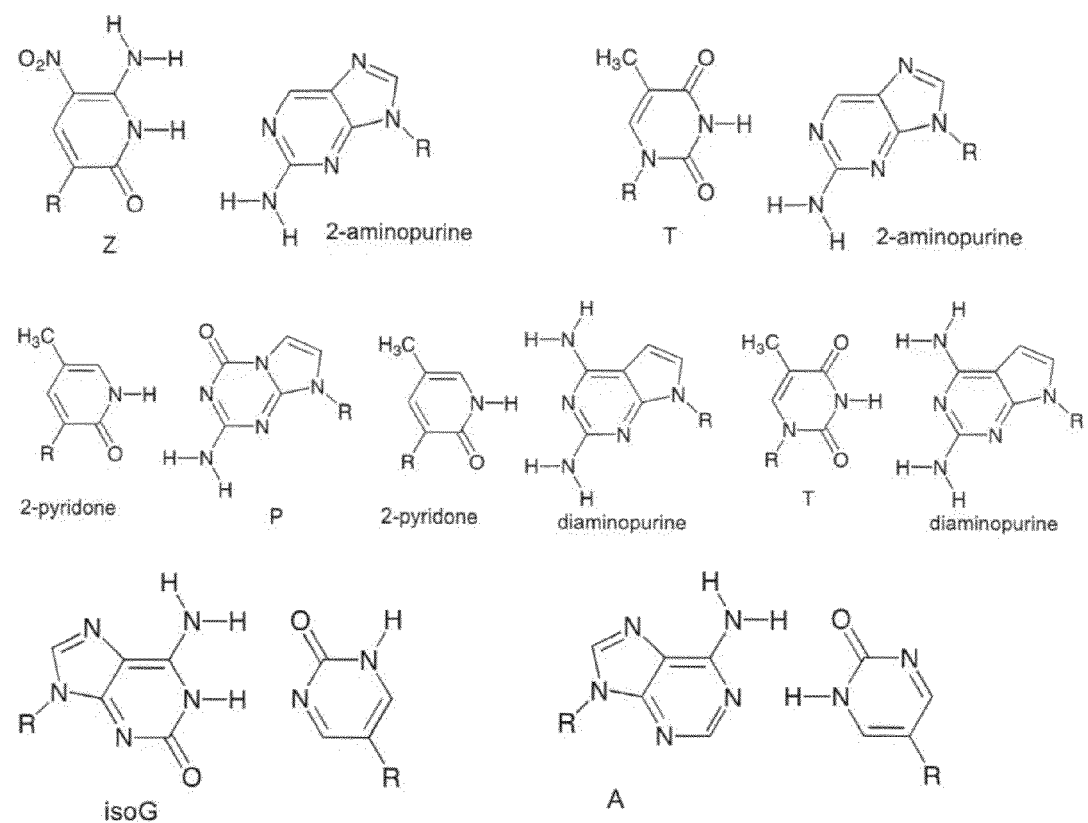

FIG. 5. Nucleobases structured to place non-standard nucleotides in a polymerase-generated product opposite specific standard nucleotides exploiting a nucleobase that presents two hydrogen bond that a standard and non-standard base have in common.

Figure 6:
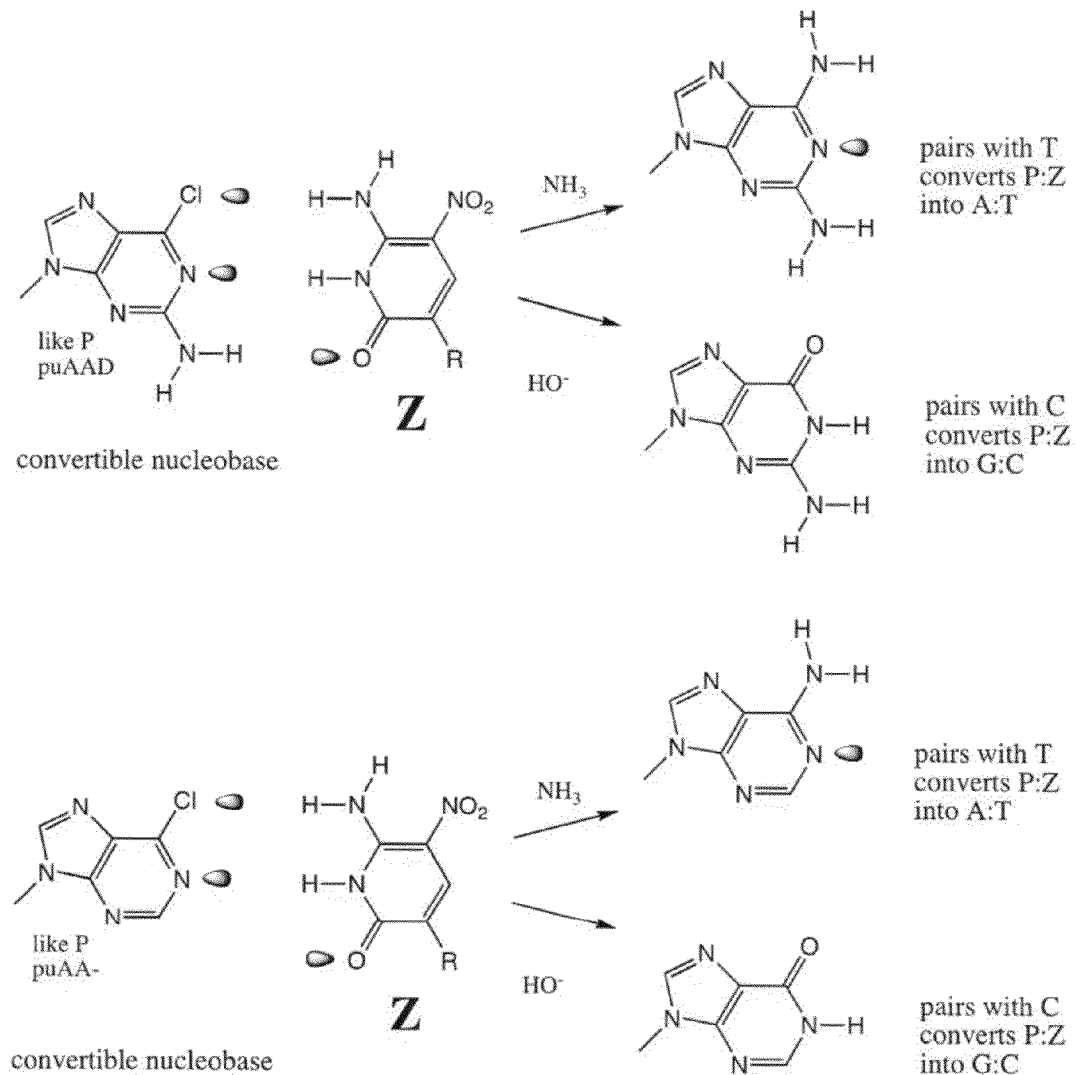

FIG. 6. Nucleobases structured to place standard nucleotides in a polymerase-generated product opposite specific non-standard nucleotides exploiting a nucleobase that complements the non-standard base that, upon subsequent treatment with chemical reagents, can generate two different standard nucleobases. This allows the products to be cloned, and further allows one to compare the sequences in the cloned products to decide where the non-standard nucleotides originally were.

Figure 7:
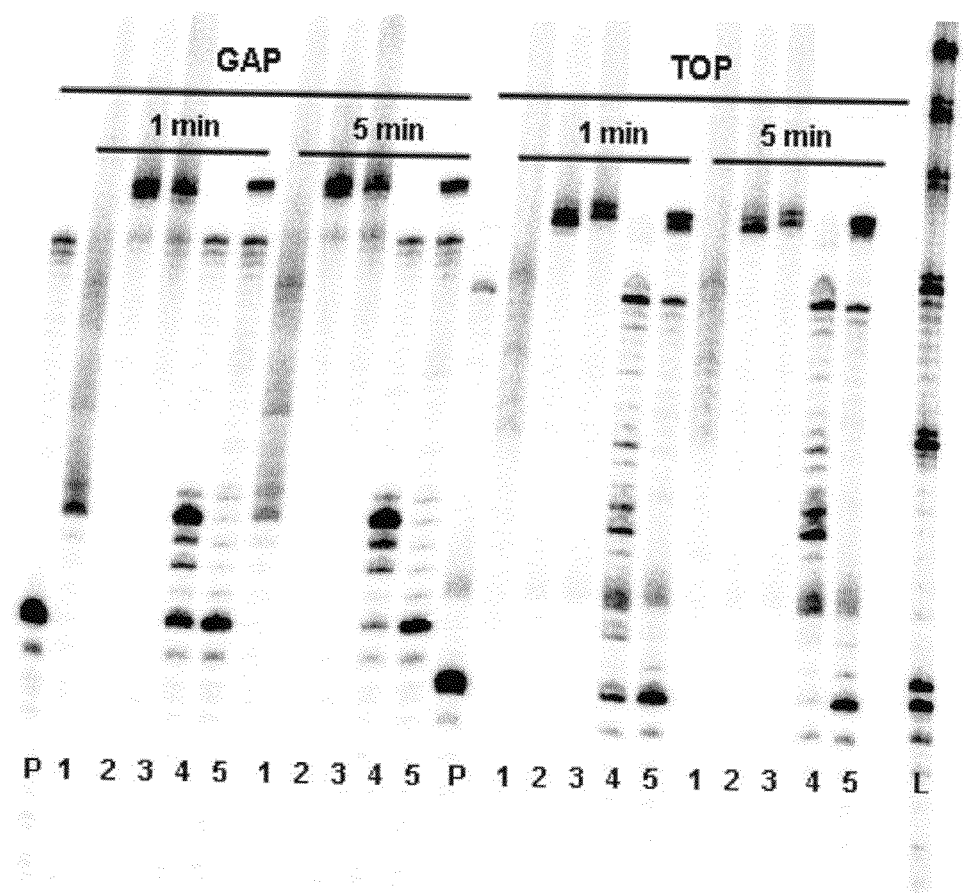
Figure 8:
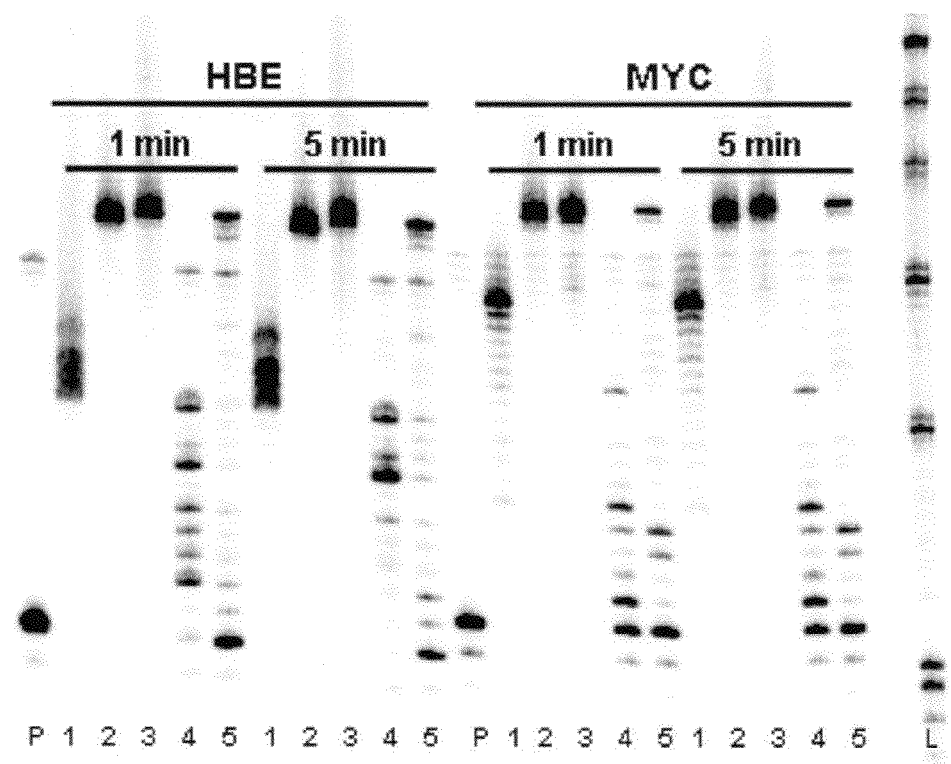
Figure 9:
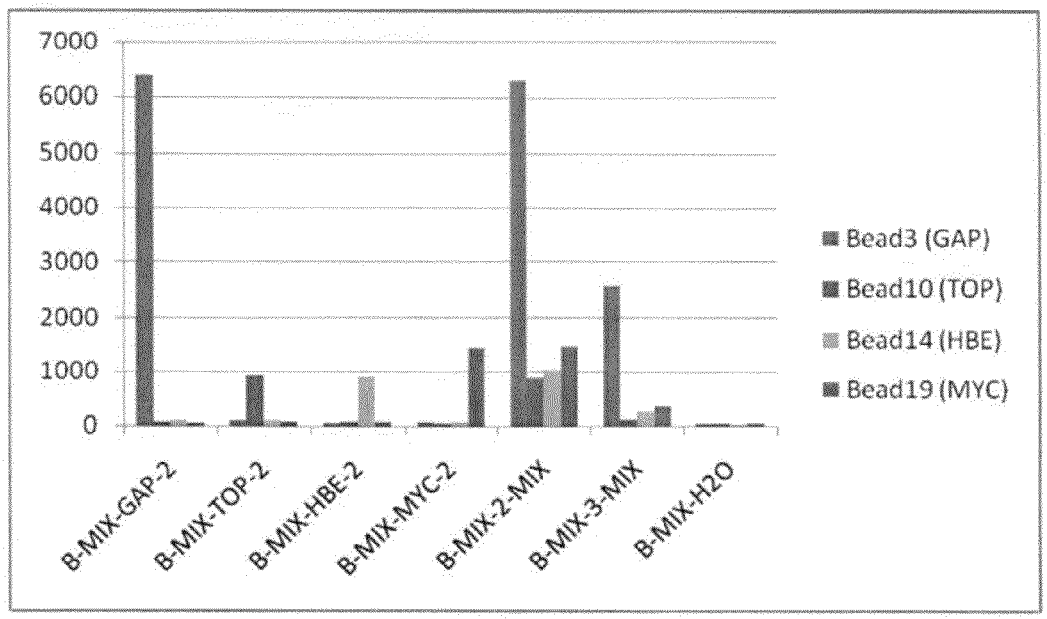
Figure 9:
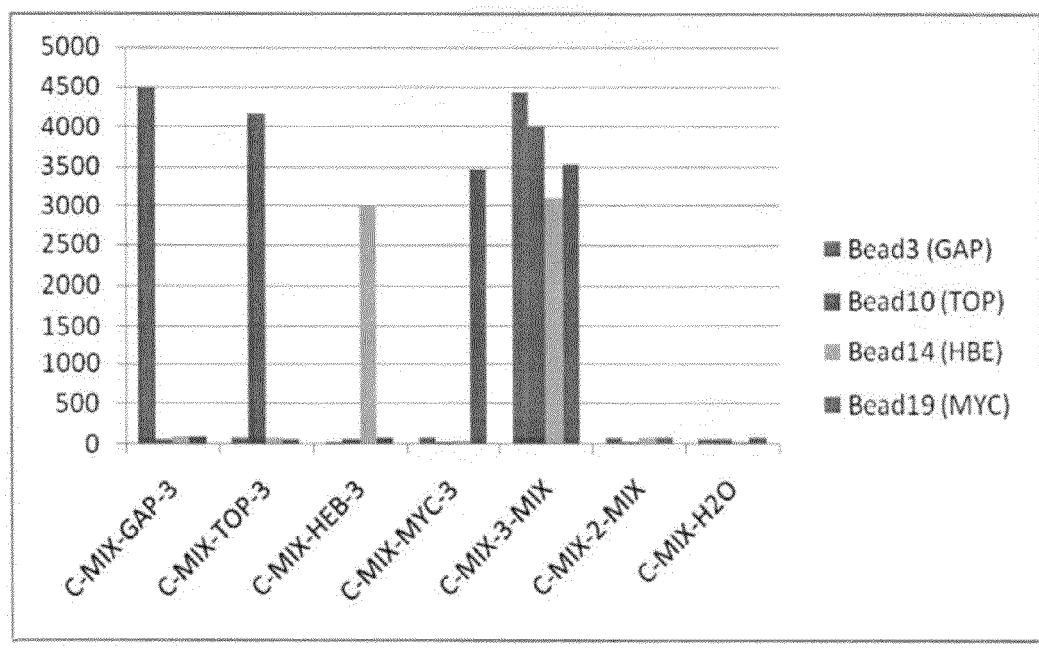
Figure 10:
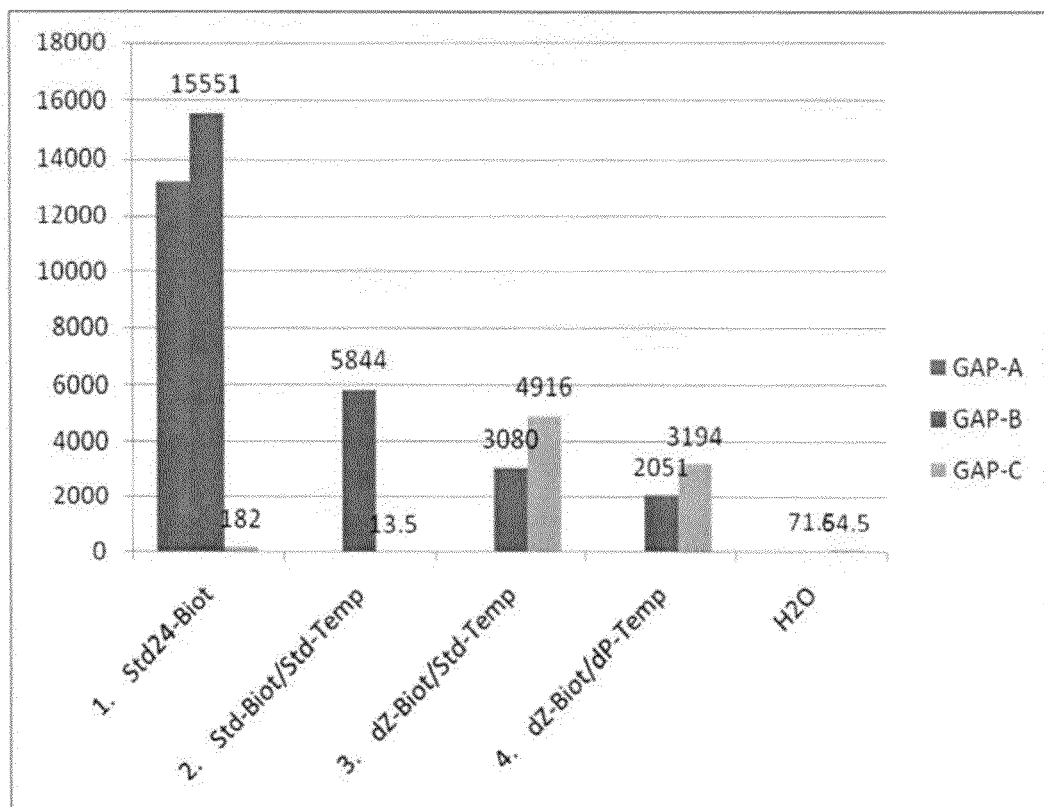
Figure 10:
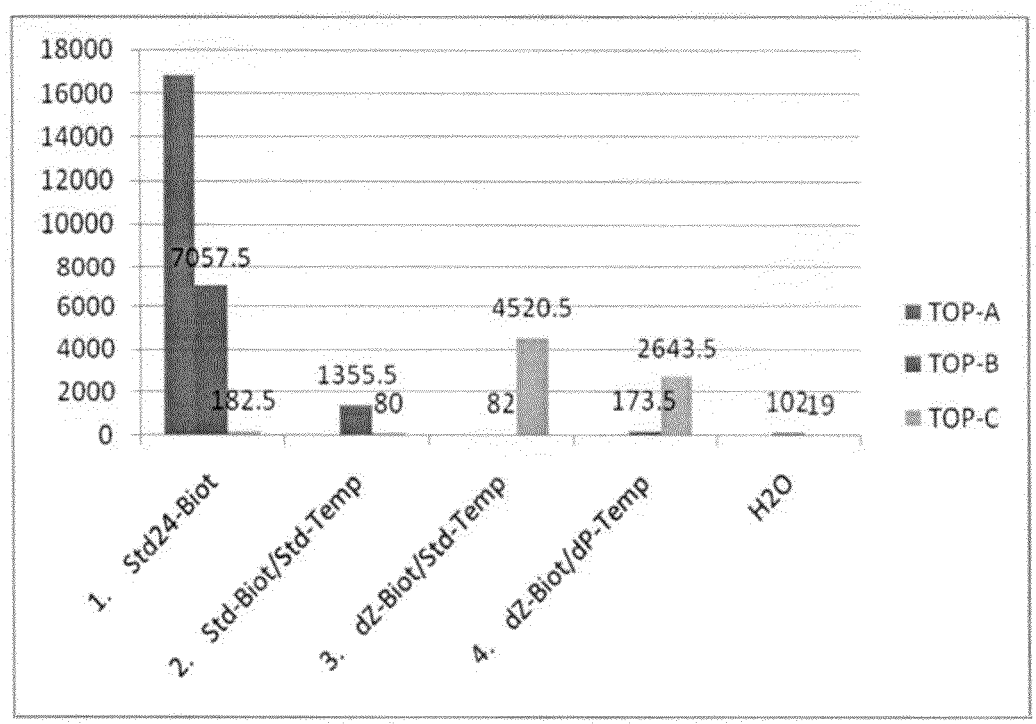
Figure 11:
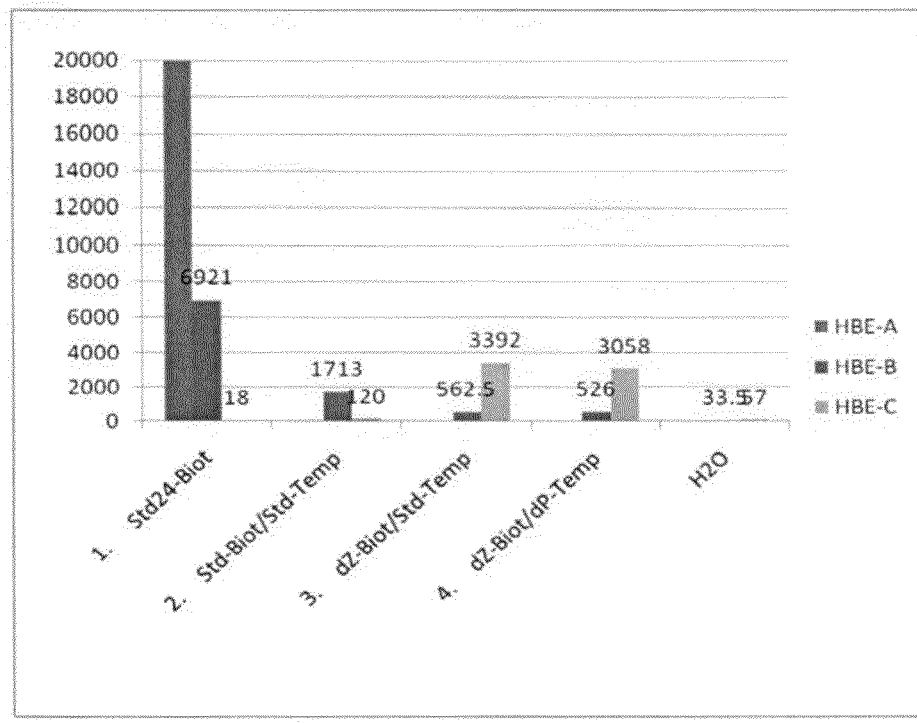
Figure 11:
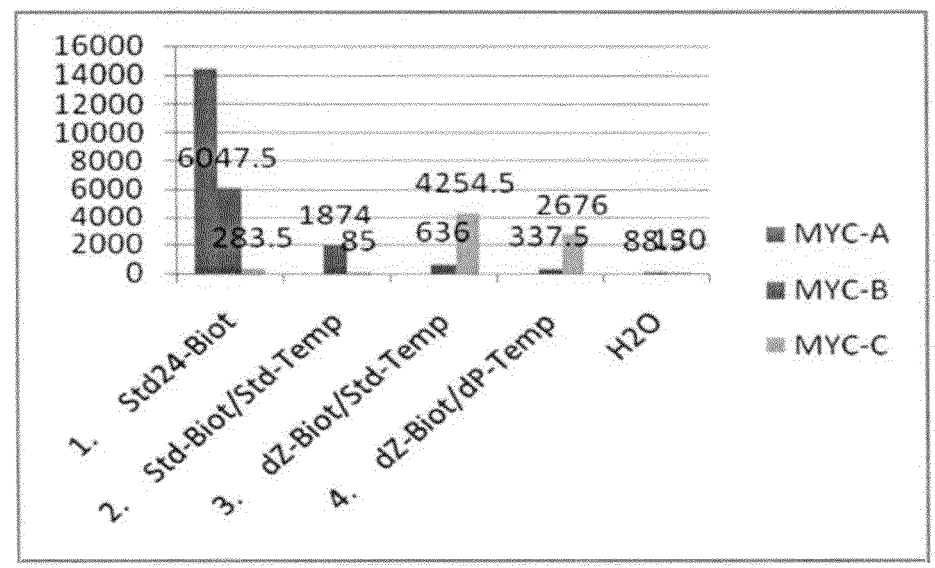
Figure 12:
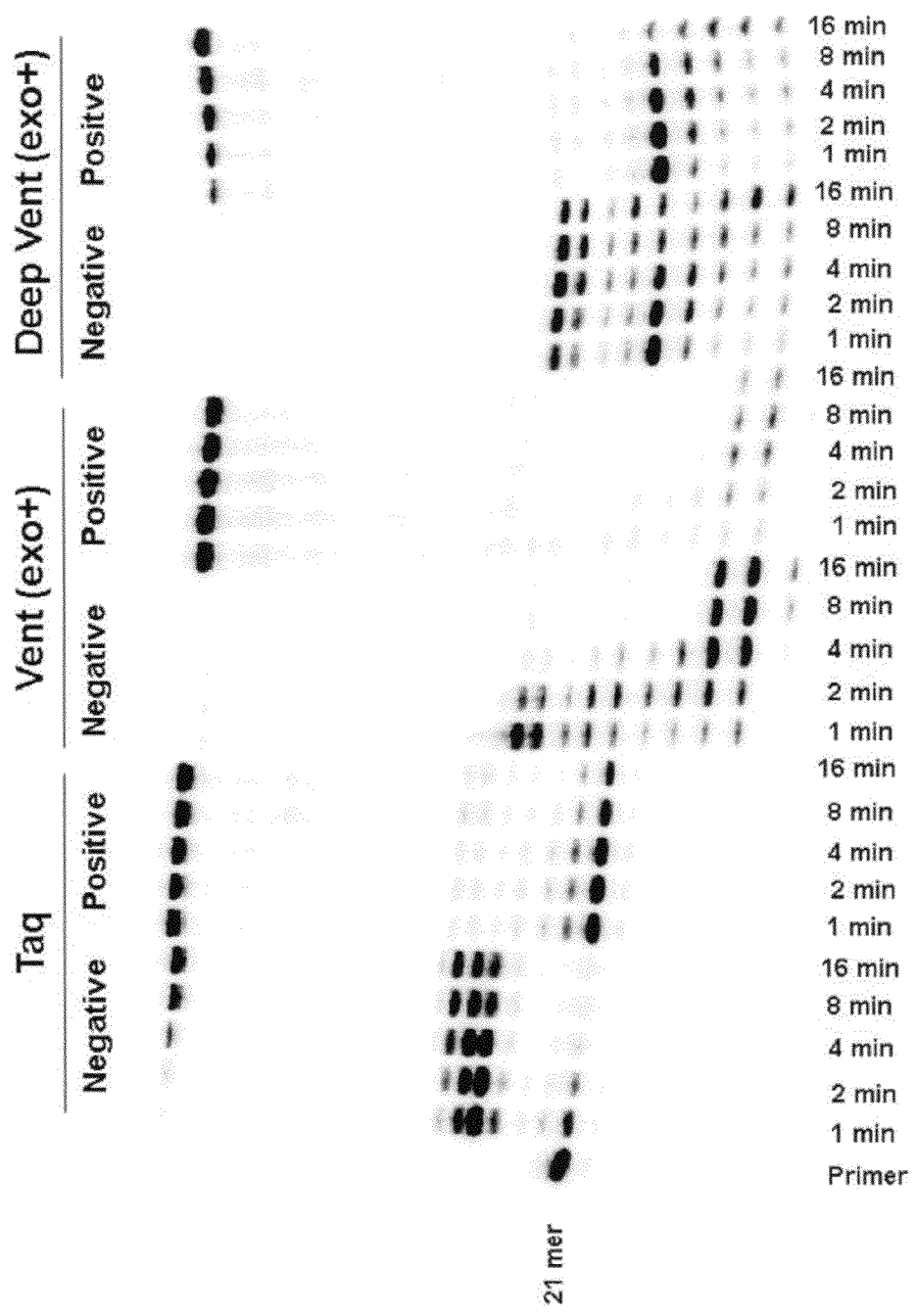
Figure 13:
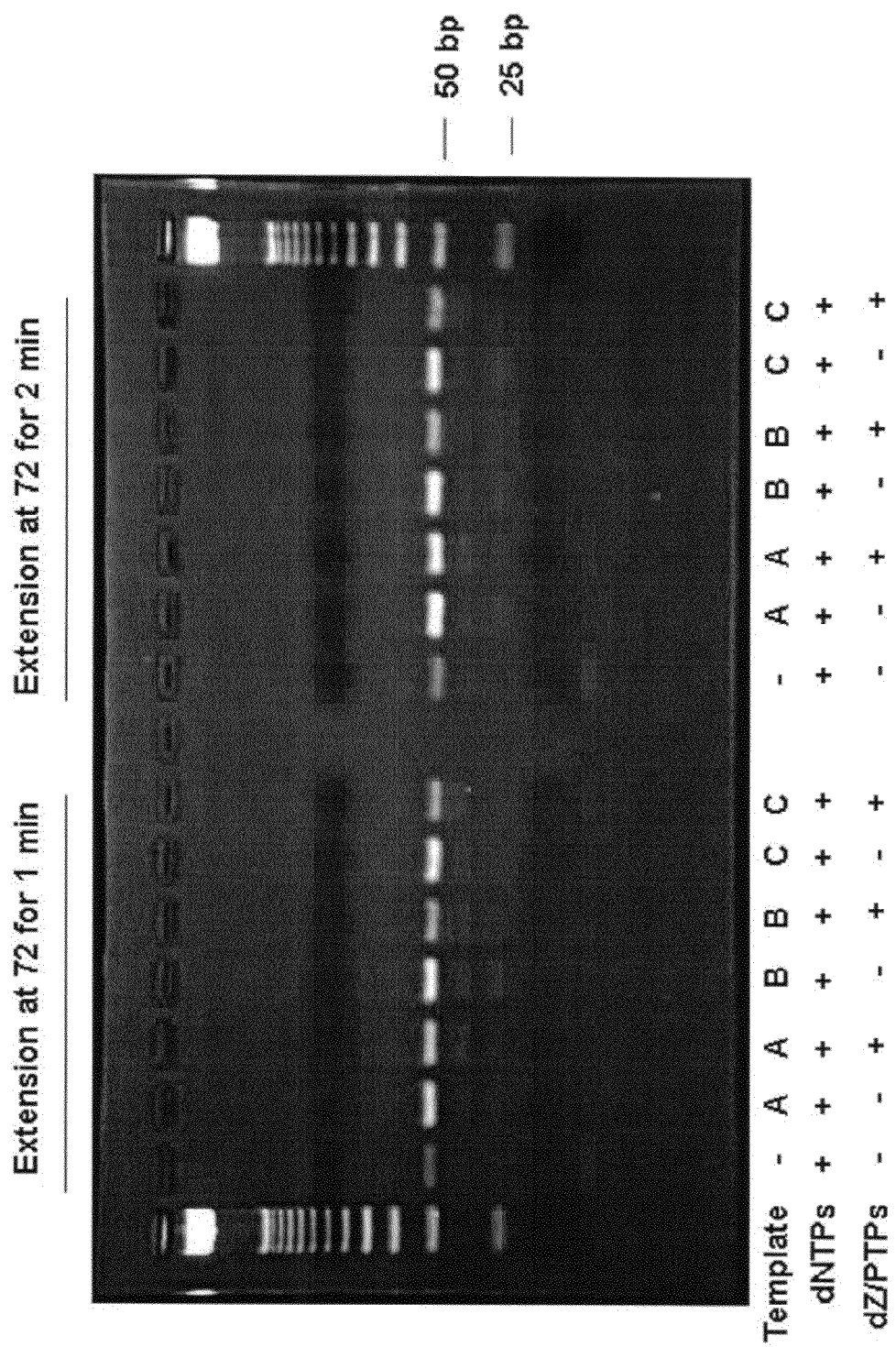

FIG. 7. Results of experiments in Example 1.
FIG. 8. Results of experiments in Example 1.
FIG. 9. Results of experiments in Example 2.
FIG. 10. Results of experiments in Example 3.
FIG. 11. Results of experiments in Example 3.
FIG. 12. Results of experiments in Example 4.
FIG. 13. Results of experiments in Example 5.

DETAILED DESCRIPTION OF THE INVENTION

Narrative

Prior to the instant invention, tags containing non-standard nucleotides were added to natural sequences (see as two examples [Elb04a][Elb04b]) by chemical synthesis, ligation, and by extension of a chimeric primer whose 5'-portion was included tags containing non-standard nucleotides (and therefore could never be fully complementary to any natural sequence) and whose 3'-end was complementary to a preselected natural sequence. If the tagged oligonucleotide was a primer, then template directed primer extension from that chimeric primer generated a product that was complementary to the natural sequence but that carried a 5'-AEGIS tag. This tag could be captured orthogonally, bringing with it the complement of the preselected natural sequence. In this way, all of the benefits of orthogonal capture based on the AEGIS alphabet could be realized with a natural analyte sequence.

The instant invention provides processes that introduce non-standard nucleobases not as tags, but within the oligonucleotide product that is semi-complementary to the original nucleotide. In the sense where it is used here, a semi-complementary oligonucleotide is an oligonucleotide that is fully complementary in the Watson-Crick sense to a reference standard oligonucleotide except at sites where standard nucleotides are mismatched with non-standard nucleotides. In the sense where it is used here, a semi-identical oligonucleotide is an oligonucleotide that is fully identical to a reference standard oligonucleotide except at sites where standard nucleotides are replaced by non-standard nucleotides. It is taught that a semi-identical oligonucleotide can be prepared from a semi-complementary oligonucleotide by copying the first by a polymerase in a process where non-standard nucleotides are matched with non-standard complements. Practically, the compositions of the instant invention are practically useful when the distance between the first and last semi-complementary pair in the semi-complementary duplex is at least 5 nucleotides, where the intervening nucleotides may be standard or non-standard.

The first inventive step in creating these processes was to set aside the prohibition in the art against mismatching, to recognize that mismatches introduced by polymerase copying might be useful.

The next inventive step recognized that polymerases may be involved in processes that end up creating replicates or complements where standard components are replaced by non-standard components with sequence specificity, or where non-standard components are replaced by standard components (the vice versa process is also achievable in this way, and in the ways described below). It was recognized that this could be done in two ways. In the first, the non-standard nucleotide is directly incorporated opposite a standard nucleotide. In the second, an intermediary nucleotide, having a structure that is neither standard or, in the sense used here, non-standard, might be incorporated opposite the standard nucleotide to give an intermediary oligonucleotide product, and the intermediary oligonucleotide product can be copied using a polymerase and the appropriate triphosphates to give a final product that contains the canonical non-standard nucleotide(s).

Several ways to achieve such replacement were then recognized as further inventive steps. Consider first the direct incorporation of a non-standard nucleotide opposite a standard nucleotide. The nucleobases can be either bases or acids, and therefore adopt protonated and deprotonated forms, respectively. In these protonated and deprotonated forms, the hydrogen bonding pattern that is presented to the complementary nucleobases is different from in the normal form. For example (FIG. 3), while the pyDDA nucleobase implemented as 6-amino-3-(2'-deoxy)-D-ribofuranosyl)-5-nitro-1H-pyridin-2-one (dZ) is complementary to the puAAD nucleobase implemented as 2-amino-1,9-dihydro-5-aza-3,7-dideaza-9-(1'-beta-D-2'-deoxyribofuranosyl)-1H-purin-6-one, also known as7-amino-9-(1'-beta-D-2'-deoxyribofuranosyl)-imidazo[1,2-c]pyrimidin-5(1H)-one (dP), its deprotonated form is complementary to G (puADD). Likewise, while the puAAD nucleobases is complementary to the pyDDA nucleobase, its protonated form is complementary to C (pyDAA).

Conditions can be adjusted to facilitate this. While not wishing to be bound by theory, mismatches between dP and standard nucleotides and mismatches between dZ and standard nucleotides do not arise from minor tautomeric forms of non-standard and standard nucleobases, but rather by their protonation and deprotonation. Specifically, protonation on the puAAD dP heterocycle generates a species that is complementary to C. Conversely, protonation of dC creates a protonated nucleotide that is Watson-Crick complementary to dP. Under this mechanism, low pH favors the dC:dP mismatch. Experimental studies showed that this was the case; dP is incorporated opposite dC at lower pH (FIG. 3).

Likewise, deprotonation of the pyDDA heterocycle generates a species that is complementary to G. Conversely, deprotonation of dG generates a species that is Watson-Crick complementary to dZ. Under this mechanism, high pH favors the dZ mismatch. Experimental studies showed that this was the case; dP is incorporated opposite dC at lower pH (FIG. 3).

Experimental work showed that if the pH is adjusted accordingly, and if a primer extension reaction is performed without dCTP or dGTP respectively, dZ is incorporated opposite template dG and dP is incorporated opposite template dC at high and low pHs, respectively. In the example above, the sequence 5'-ATGCTTAC-3' generates a copy having the sequence 5'-GTAAGZAT-3' and 5'-PTAAPCT-3'. A screen of polymerases identified several that would do this efficiently, including incorporating non-standard components consecutively opposite the same standard component presented consecutively in the template.

Thus, if a polymerase is provided with dZTP and no dGTP, then copying a template at an appropriate pH should generate a product where dZ is incorporated opposite dG (where dC would normally be incorporated). Correspondingly, if a polymerase is provided with dPTP and no dCTP, then copying a template at an appropriate pH should generate a product where dP is incorporated opposite dC (where dG would normally be incorporated). These can be captured onto (for example) a Luminex bead or an array with complementary puAAD- or pyDDA-containing capture oligonucleotides (respectively), allowing the full benefit of the orthogonality of an expanded genetic alphabet in that capture process. This produces the replacement in a single polymerase extension.

This can also be done by direct replacement if the non-standard nucleobase has a minor tautomeric form that is complementary to the standard nucleobase. This can be done through incubations that lacked the standard nucleoside triphosphate complement, or by doing template-directed primer extension under conditions adjusted so as to favor the mismatch. For example, if an analyte is used as a template in a primed polymerase reaction where isoG is presented as a triphosphate without dATP, an oligonucleotide with a defined sequence (for illustration, let us choose an arbitrary sequence that is shorter than one that would be useful, but is sufficiently short as to not require a sequence listing, 5'-ATGCTTAC-3'), one would generate the product 5'-GT(isoG)(isoG)GC(isoG)T-3'. This would be captured on a probe containing the non-standard sequence 5'-A(isoC)GC(isoC)(isoC)AC-3'. Thus, the analyte would lead to a specific orthogonal sequence without the need for a tag.

A second way to achieve a replacement is to use an intermediary nucleobase. For example, that intermediary nucleobase may be structured to have more than one tautomeric form, where in one tautomeric form, the nucleobases is complementary to a standard nucleobases, and is, in its other tautomeric form complementary to a non-standard nucleobases. For example (FIG. 4), the aminopyrimidinone nucleobase labeled J (to indicate the 2'-deoxy-1-methylpseudocytidine implementation) in one of its tautomeric forms is complementary to dG. In its other tautomeric form, J is complementary to P (see [Kim09], whose content is fully incorporated herein through citation). Thus, if a polymerase is provided with dJTP and no dCTP, then copying a template at any pH generates a product where dJ is incorporated opposite dC (where dG would normally be incorporated). The product oligonucleotide might be directly captured by a P-containing oligonucleotide, again allowing the full benefit of the orthogonality of an expanded genetic alphabet in that capture process, again producing the replacement in a single polymerase cycle. Alternatively, the J-containing oligonucleotide product may be treated as an intermediary, and copied with dPTP to obtain a replicate of the original oligonucleotide where dG's are replaced by dP's. The vice versa process using dJTP creates, after two polymerase extensions, derived oligonucleotides where the Z:P pairs have been replaced by C:G pairs. Such derived oligonucleotides can be cloned and sequenced using standard methods.

A third approach recognizes that in some cases, a non-standard nucleobase and a standard nucleobase share two of the three hydrogen bonding groups. Accordingly, this approach structures an intermediary nucleobase to form just two hydrogen bonds with its complement, where the two hydrogen bonding groups that it forms are those to the hydrogen bonding groups that the non-standard nucleobase and a standard nucleobases share. For example (FIG. 5), 2-aminopurine can form two hydrogen bonds to both the non-standard dZ and to the standard dT. The dZ and dT hydrogen bonding patterns differ only in their hydrogen bonding group in the major groove, and 2-aminopurine does not present any hydrogen bonding group at all in this position. Likewise, 2-pyridone presents hydrogen bonding units to the hydrogen bonding elements that dP and diaminopurine have in common.

A fourth approach would exploit a chemically convertible intermediate nucleoside, one where the attached nucleobases is incorporated opposite the non-standard nucleobases. Then, a chemical step converts this nucleobase to a nucleobase that is Watson-Crick complementary to a non-standard nucleobase. For example, 2-amino-6-chloropurine (FIG. 6), who 2'-deoxynucleoside triphosphate is commercially available, presents a hydrogen bond acceptor-acceptor-donor pattern to its complement; it is therefore incorporated by a DNA polymerase opposite dZ (pyDDA). Once incorporated, known procedures, incorporated herein by reference [Tan06] [Mur91], convert it to either puADD (guanine, complementary to dC) or puDAD (diaminopurine, complementary to dT) by treatment with hydroxide or ammonia, respectively. Indeed, if the desire is to retain information about where the dZ was in the parent oligonucleotide, it can be treated with methanolic ammonium hydroxide with water present in an amount to create approximately equal amounts of guanine and diaminopurine.

Various of these strategies can be combined. For example, 6-chloropurine presents a puAA-hydrogen bonding pattern that is complementary to the "top" (nearest the major groove) hydrogen bonding units of dZ (or other implementations of the pyDDA hydrogen bonding pattern), and can be converted with ammonia into A, or with hydroxide into inosine, which is a complement to C. This has the net effect of converting a Z:P pair into either a C:G pair or a T:A pair in the products of successive polymerase copying, allowing these to be cloned. Further comparison of the products allows one to infer the position of the Z:P pair in the original oligonucleotide. The advantage of 6-chloropurine over 2-amino-6-chloropurine is that the first can be converted under milder conditions.

Given this process, one of ordinary skill in the art can recognize multiple architectures for assays that use non-standard nucleotides and their orthogonality to detect natural oligonucleotides of specific sequence with extremely high signal-noise ratios. For example, an analyte can be amplified using PCR primers as normal designed to generate a particular product. As is well known in the art, to some extent, non-target DNA sequences will be amplified as well, if they are present in the complex biological mixture. If a capture sequence is introduced as a tag, these undesired amplicons will also be tagged.

LITERATURE CITED

[Bro97] Brownie, J., Shawcross, S., Theaker, J., Whitcombe, D., Ferrie, R., Newton, C., Little, S. (1997). The elimination of primer-dimer accumulation in PCR. *Nucleic Acids Res.* 25, 3235-3241

[Elb04a] Elbeik, T., Markowitz, N., Nassos, P., Kumar, U., Beringer, S., Haller, B. and Ng, V. (2004) Simultaneous runs of the Bayer VERSANT HIV-1 version 3.0 and HCV bDNA version 3.0 quantitative assays on the system 340 platform provide reliable quantitation and improved work flow. *J. Clin. Microbiol.*, 42, 3120-3127.

[Elb04b] Elbeik, T., Surtihadi, J., Destree, M., Gorlin, J., Holodniy, M., Jortani, S. A., Kuramoto, K., Ng, V., Valdes, R., Valsamakis, A. et al. (2004) Multicenter evaluation of the performance characteristics of the Bayer VERSANT HCV RNA 3.0 assay (bDNA). *J. Clin. Microbiol.*, 42, 563-569.

[Hor95] Horlacher, J., Hottiger, M., Podust, V. N., Hübscher, U., Benner, S. A. (1995) Expanding the genetic alphabet: Recognition by viral and cellular DNA polymerases of nucleosides bearing bases with non-standard hydrogen bonding patterns. *Proc. Natl. Acad. Sci.*, 92, 6329-6333

[Hut03] Hutter, D. and Benner, S. A. (2003) Expanding the genetic alphabet. Non-epimerizing nucleoside with the pyDDA hydrogen bonding pattern. *J. Org. Chem.*, 68, 9839-9842

[Joh04] Johnson, S. C., Sherrill, C. B., Marshall, D. J., Moser, M. J., Prudent, J. R. (2004) A third base pair for the polymerase chain reaction: inserting isoC and isoG. *Nucleic Acids Res.* 32, 1937-1941

[Jur00] Jurczyk, S. C., Horlacher, J., Devine, K. G., Benner, S. A., Battersby, T. R. (2000) Synthesis and characterization of oligonucleotides containing 2'-deoxyxanthosine using phosphoramidite chemistry. *Helv. Chim. Acta* 83, 1517-1524

[Jur98] Jurczyk, S., Kodra, J. T., Rozzell, J. D., Jr., Benner, S. A., Battersby, T. R. (1998) Synthesis of oligonucleotides containing 2'-deoxyisoguanosine and 2'-deoxy-5-methyl-iso-cytidine using phosphoramidite chemistry. *Helv. Chim. Acta* 81, 793-811]

[Jur99] Jurczyk, S. C., Battersby, T. R., Kodra, J. T., Park, J.-H., Benner, S. A. (1999) Synthesis of 2'-deoxyisoguanosine triphosphate and 2'-deoxy-5-methyl-isocytidine triphosphate. *Helv. Chim. Acta.* 82, 1005-1015

[Kim09] Kim, H. J., Leal, N. A., Benner, S. A. (2009) 2'-Deoxy-1-methylpseudocytidine, a stable analog of 2'-deoxy-5-methylisocytidine. *Bioorg Med. Chem.* 17, 3728-373

[Kod97] Kodra, J., Benner, S. A. (1997) Synthesis of an N-alkyl derivative of 2'-deoxyisoguanosine. *Syn. Lett.*, 939-940

[Lut99] Lutz, S., Burgstaller, P., Benner, S. A. (1999) An in vitro screening technique for polymerases that can incorporate modified nucleotides. Pseudouridine as a substrate for thermostable polymerases. *Nucl. Acids Res.* 27, 2792-2798]

[Mar04] Martinot, T. A., Benner, S. A. (2004) Expanding the genetic alphabet: 7-Deaza-isoguanosine favors the 1N—H keto form by $10^3$-to-1 over the enol. *J. Org. Chem.* 69, 3972-3975

[Mur91] Murakami, K., Shirasaka, T., Yoshioka, H., Kojima, E., Aoki, S., Ford, Jr., H., Driscoll, J. S., Kelley, J. A., Mitsuya, H. (1991) *Escherichia coli* mediated biosynthesis and in vitro Anti-HIV Activity of lipophilic 6-Halo-2',3'-dideoxypurine nucleosides. *J. Med. Chem.* 34, 1606-1612

[Pic90] Piccirilli, J. A., Krauch, T., Moroney, S. E., Benner, S. A. (1990) Extending the genetic alphabet. Enzymatic incorporation of a new base pair into DNA and RNA. *Nature* 343, 33-37

[Pic91] Piccirilli, J. A., Krauch, T., MacPherson, L. J., Benner, S. A. (1991) A direct route to 3-(ribofuranosyl)-pyridine nucleosides. *Helv. Chim. Acta* 74, 397-406

[Sep76] Sepiol, J., Kazimierczuk, Z., Shugar, D. Z. (1976) Tautomerism of iso-guanosine and solvent-induced keto-enol equilibrium. *Z. Naturforsch* 31C, 361-370

[Sis05] Sismour, A. M., Benner, S. A. (2005) The use of thymidine analogs to improve the replication of an extra DNA base pair: A synthetic biological system. *Nucl. Acids Res.* 33, 5640-5646

[Swi89] Switzer, C. Y., Moroney, S. E., Benner, S. A. (1989) Enzymatic incorporation of a new base pair into DNA and RNA. *J. Am. Chem. Soc.* 111, 8322-8323

[Swi93] Switzer, C. Y., Moroney, S. E., Benner, S. A. (1993) Enzymatic recognition of the base pair between iso-cytidine and iso-guanosine. *Biochemistry* 32, 10489-10496

[Tan06] Tang, Y., Ramaiah, M., Vince, R. (2006) Synthesis and biological evaluation of carboacyclic nucleosides with (Z) and (E)-9-[4,4-bis(hydroxymethyl)]-2-butenyl side chain. *Bioorg. Med. Chem. Lett.* 14, 5866-5875

[Voe93] Voegel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547

[Voe96a] Voegel, J. J., Benner, S. A. (1996) Synthesis and characterization of non-standard nucleosides and nucleotides bearing the acceptor-donor-donor pyrimidine analog 6-amino-3-methylpyrazin-2-one. *Helv. Chim. Acta* 79, 1863-1880

[Voe96b] Voegel, J. J., Benner, S. A. (1996) Synthesis, molecular recognition & enzymology of oligonucleotides containing the non-standard base pair between 5-aza-7-deaza-iso-guanine & 6-amino-3-methylpyrazin-2-one, a donor-acceptor-acceptor purine analog and an acceptor-donor-donor pyrimidine analog. *Helv. Chim. Acta* 79, 1881-1898

[Von95] von Krosigk, U., Benner, S. A. (1995) pH-independent triple helix formation by an oligonucleotide containing a pyrazine donor-donor-acceptor base. *J. Am. Chem. Soc.* 117, 5361-5362

[Yan06] Yang, Z., flutter, D., Sheng, P., Sismour, A. M. and Benner, S. A. (2006) Artificially expanded genetic information system. A new base pair with an alternative hydrogen bonding pattern. *Nucleic Acids Res.*, 34, 6095-6101.

[Yan07] Yang, Z., Sismour, A. M., Sheng, P., Puskar, N. L., Benner, S. A. (2007) Enzymatic incorporation of a third nucleobase pair. *Nucl. Acids Res.* 35, 4238-4249

EXAMPLES

Patent AEGIS Convert Examples Provenance

To demonstrate the steps of the instant invention, a pair of nucleoside analogs that contain hereocycles that implement the pyDDA hydrogen bonding pattern on an aminopyridone skeleton (dZ) and that implement the puAAD hydrogen bonding pattern in 2-amino-1,9-dihydro-5-aza-3,7-dideaza-9-(1'-beta-D-2'-deoxyribofuranosyl)-1H-purin-6-one (dP) were examined. These two heterocycles are complementary in the Watson-Crick sense, in that the large dP is size complementary to the small dZ, and the hydrogen bond donating and accepting groups of dP complement those of dZ when the two are paired in a standard Watson-Crick double helix.

Example 1

Purpose

Incorporating dZ into oligonucleotides opposite dG via primer extension using THERMINATOR™ DNA polymerase.

Summary of the Results:

The dZ containing oligo can be efficiently generated through primer extension using standard template and THERMINATOR™ DNA polymerase. These data are shown in FIG. 7 and FIG. 8.

Oligonucleotides Used in this Example:
Oligonucleotides for glyceraldehyde-3-phosphate dehydrogenase (GAP)
Lua3-Std24-Biot:
3'-CTA ACA TTC TAA ACT ATT TCA CAT-Biot-5' SEQ. ID. NO. 1
3'-CTA ACA TTC TAA ACT ATT TCA CAT-GGACTG-GACGGCAGATCTTTT-Biot-5' SEQ. ID. NO. 2
GAP-prim-21-Biot: 3'-ZTA AZA TTZ TAA AZT ATT TZA ZAT-GGACTGGACGGCAGATCTTTT-Biot-5' SEQ. ID. NO. 3
GAP-F-Std45: 5'-GAT TGT AAG ATT TGA TAA AGT GTA CCTGACCTGCCGTCTAGAAAA-3' SEQ. ID. NO. 4
GAP-prim-21-Biot: 3'-CTA AZA TTZ TAA AZT ATT TZA ZAT-GGACTGGACGGCAGATCTTTT-Biot-5' SEQ. ID. NO. 5
GAP-F-45-5P: 5'-GAT TPT AAP ATT TPA TAA APT PTA CCTGACCTGCCGTCTAGAAAA-3' SEQ. ID. NO. 6
Oligonucleotides for Topoisomerase (TOP)
Lua10-Std24-Biot: 3'-ACA TCT AAA CAT ACA TAC ATA CTA-Biot-5' SEQ. ID. NO. 7
3'-ACA TCT AAA CAT ACA TAC ATA CTA-CT-GTCGGGGCCTACTCTTG-Biot-5' SEQ. ID. NO. 8
TOP-prim-19-Biot: 3'-AZA TZT AAA ZAT AZA TAZ ATA ZTA-CTGTCGGGGCCTACTCTTG-Biot-5' SEQ. ID. NO. 9
Top-F-Std43: 5'-TGT AGA TTT GTA TGT ATG TAT GAT GACAGCCCCGGATGAGAAC-3' SEQ. ID. NO. 10
TOP-prim-19-Biot: 3'-ACA TZT AAA ZAT AZA TAZ ATA ZTA-CTGTCGGGGCCTACTCTTG-Biot-5' SEQ. ID. NO. 11
Top-F-43-5P: 5'-TGT APA TTT PTA TPT ATP TAT PAT GACAGCCCCGGATGAGAAC-3' SEQ. ID. NO. 12
Oligonucleotides for Human Epidermal Growth Factor (HBE)
Lua14-Std24-Biot: 3'-TTT CAT ATC ATT CTA CAT ATC ATC-Biot-5' SEQ. ID. NO. 13
3'-TTT CAT ATC ATT CTA CAT ATC ATC-CGGGGT-CAACGGCAGATCCT-Biot-5' SEQ. ID. NO. 14
HBE-prim-20-Biot: 3'-TTT ZAT ATZ ATT ZTA ZAT ATZ AT-CGGGGTCAACGGCAGATCCT-Biot-5' SEQ. ID. NO. 15
HBE-F-Std43: 5'-AAA GTA TAG TAA GAT GTA TAG TA GCCCCAGTTGCCGTCTAGGA-3' SEQ. ID. NO. 16
HBE-prim-20-Biot: 3'-TTT ZAT ATZ ATT ZTA ZAT ATZ AT-CGGGGTCAACGGCAGATCCT-Biot-5' SEQ. ID. NO. 15
HBE-F-43-5P: 5'-AAA PTA TAP TAA PAT PTA TAP TA GCCCCAGTTGCCGTCTAGGA-3' SEQ. ID. NO. 19
Oligonucleotides for the Myc Gene (MYC)
Lua19-Std24-Biot: 3'-CAT AAA CTC ATT CAT TAA CTA ACT-Biot-5' SEQ. ID. NO. 18
3'-CAT AAA CTC ATT CAT TAA CTA ACT-AGGAG-GAATACGGAGATAGTA-Biot-5' SEQ. ID. NO. 19
MYC-prim-21-Biot: 3'-ZAT AAA ZTZ ATT ZAT TAA ZTA AZT-AGGAGGAATACGGAGATAGTA-Biot-5' SEQ. ID. NO. 20
MYC-F-Std45: 5'-GTA TTT GAG TAA GTA ATT GAT TGA TCCTCCTTATGCCTCTATCAT-3' SEQ. ID. NO. 21
MYC-prim-21-Biot: 3'-CAT AAA ZTZ ATT ZAT TAA ZTA AZT-AGGAGGAATACGGAGATAGTA-Biot-5' SEQ. ID. NO. 22
MYC-F-45-5P: 5'-GTA TTT PAP TAA PTA ATT PAT TPA TCCTCCTTATGCCTCTATCAT-3' SEQ. ID. NO. 23

| Protocol for the primer extension: | | | | | |
|---|---|---|---|---|---|
| | 1 | 2 | 3 | 4 | 5 |
| γ-$^{32}$P-Primer (1 μM) | 0.1 μL | 0.1 μL | 0.1 μL | 0.1 μL | 0.1 μL |
| Biotin-Primer (1 μM) | 2 μL | 2 μL | 2 μL | 2 μL | 2 μL |
| Template (2 μM) | 1.5 μL Std-Temp | 1.5 μL Std-Temp | 1.5 μL Std-Temp | 1.5 μL dP-Temp | 1.5 μL dP-Temp |
| 10x Thermopol Buffer (pH 9.0) | 1 μL | 1 μL | 1 μL | 1 μL | 1 μL |
| dNTP (1 mM) | 1 μL dA, T, G/TP | 1 μL dNTP | 1 μL dA, T, G, | 1 μL dNTP | 1 μL dNTP + dZTP |
| DNA polymerase (1 U/μL) | 1 μL Therminator | 1 μL Therminator | 1 μL Therminator | 1 μL Taq | 1 μL Taq |
| H$_2$O (final volume of 10 μl) | 3.5 μL | 3.5 μL | 3.5 μL | 3.5 μL | 3.5 μL |

Note:
1 (negative control): Therminator, dATP + dTTP + dGTP;
2 (positive control): Therminator, dATP + dTTP + dGTP + dCTP;
3 (experiment): Therminator, dATP + dTTP + dGTP + dZTP;
4(negative control): Taq, dNTP;
5 (experiment): Taq, dNTP + dZTP.

Primer Extension with $^{32}$P-Labeled Primer:
5'-$^{32}$P-Labeled primer (0.1 pmole plus cold primer (biotin-primer) 2 pmole, final assay concentration 210 nM) was annealed to either standard template or dP containing template (3 pmole, final assay concentration 300 nM) in thermpol reaction buffer by heating (5 min 95° C.) and then slow cooling (0.5 h) to room temperature. dNTP and DNA polymerase were added at room temperature, followed by incubating at 72° C. for 1 min or 5 min, and then, quenched by dilution into PAGE loading/quench buffer (8 μL, 10 mM EDTA in formamide). Samples were resolved by electrophoresis using a 16% PAGE (7 M urea). The gel was analyzed using MolecularImager software.

Primer Extension without $^{32}$P Labeled Primer:
Biotin-labeled primer (2 pmole, final assay concentration 200 nM) was annealed to either standard template or dP containing template (3 pmole, final assay concentration 300 nM) in thermpol reaction buffer by heating (5 min 95° C.) and then slow cooling (0.5 h) to room temperature. The biotin-labeled primer was extended under three different conditions: 2 (positive control): Therminator, dNTP; 3 (experiment): Therminator, dATP+dTTP+dGTP+dZTP; 5 (experiment): Taq, dNTP+ dZTP. dNTP and DNA polymerase were added at room temperature, followed by incubating at 72° C. for 5 min. The reaction was quenched with 2 μL of 20 mM EDTA, and diluted with 190 μL of ddH$_2$O to give the fully extended full-length dZ containing or control oligonucleotide (final concentration 10 fmoles/μL).
1 (negative control): Therminator, dATP+dTTP+dGTP; 2 (positive control): Therminator, dATP+dTTP+dGTP+dCTP; 3 (experiment): Therminator, dATP+dTTP+dGTP+dZTP; 4 (negative control): Taq, dNTP; 5 (experiment): Taq, dNTP+ dZTP.

Example 2

Capture of the Converted Oligonucleotides on Luminex Beads

Purpose:
The method of the instant invention is especially useful if the products of the prime extension process that incorporate a non-standard nucleotide (here, dZ, implementing the pyDDA hydrogen bonding pattern) can be captured on a capture tag that is complementary, and contains dP in the oligonucleotide. This capture is "orthogonal", in the sense that no natural oligonucleotide contains either dP or dZ. Therefore, no natural nucleotide can interfere with the capture. In this experiment, three different products are captured on three different Luminex beads, to which dP-containing oligonucleotides have been attached by preparing them with a 5'-amino group using solid phase synthesis, and coupling to beads carrying —COOH groups with water-soluble carbodiimide, following standard procedures. These are visualized by their capture of a biotinylated oligonucleotide, which captures a fluorescent phycoerythrin fluor, following standard procedures described by the Luminex users manual.

Oligonucleotides Used in this Study:
B-type beads mixture: coupling standard oligo to MicroPlex COOH Beads:
GAP-F-Lu3-NH2: 5'-NH$_2$—C$_{12}$-GAT TGT AAG ATT TGA TAA AGT GTA-3' (B-Mix-GAP) SEQ. ID. NO. 24
Top-F-Lu10-NH2: 5'-NH$_2$—C$_{12}$-TGT AGA TTT GTA TGT ATG TAT GAT-3' (B-Mix-TOP) SEQ. ID. NO. 25
HBE-F-Lu14-NH2: 5'-NH$_2$—C$_{12}$-AAA GTA TAG TAA GAT GTA TAG TAG-3' (B-Mix-HBE) SEQ. ID. NO. 26
MYC-F-Lu19-NH2: 5'-NH$_2$—C$_{12}$-GTA TTT GAG TAA GTA ATT GAT TGA-3' (B-Mix-MYC) SEQ. ID. NO. 27
C-type beads mixture: coupling dP containing oligo to MicroPlex COOH Beads:
GAP-F-Lu3-NH2-5P: 5'-NH$_2$—C$_{12}$-GAT TPT AAP ATT TPA TAA APT PTA-3' (C-Mix-GAP) SEQ. ID. NO. 28
Top-F-Lu10-NH2-5P: 5'-NH$_2$—C$_{12}$-TGT APA TTT PTA TPT ATP TAT PAT-3' (C-Mix-TOP) SEQ. ID. NO. 29
HBE-F-Lu14-NH2-5P: 5'-NH$_2$—C$_{12}$-AAA PTA TAP TAA PAT PTA TAP TAG-3' (C-Mix-HBE) SEQ. ID. NO. 30
MYC-F-Lu19-NH2-5P: 5'-NH$_2$—C$_{12}$-GTA TTT PAP TAA PTA ATT PAT TPA-3' (C-Mix-MYC) SEQ. ID. NO. 31
Complementary Biotin Labeled Oligonucleotides:
GAP:
2. 3'-CTA ACA ITC TAA ACT ATT TCA CAT-GGACTG-GACGGCAGATCTTTT-Biot-5' SEQ. ID. NO. 2
GAP-F-Std45: 5'-GAT TGT AAG ATT TGA TAA AGT GTA CCTGACCTGCCGTCTAGAAAA-3' SEQ. ID. NO. 4
3. GAP-prim-21-Biot: 3'-ZTA AZA TTZ TAA AZT ATT TZA ZAT-GGACTGGACGGCAGATCTTTT-Biot-5' SEQ. ID. NO. 3

GAP-F-Std45: 5'-GAT TGT AAG ATT TGA TAA AGT GTA CCTGACCTGCCGTCTAGAAAA-3' SEQ. ID. NO. 4
TOP:
2. 3'-ACA TCT AAA CAT ACA TAC ATA CTA-CTGTCGGGGCCTACTCTTG-Biot-5' SEQ. ID. NO. 8
Top-F-Std43: 5'-TGT AGA TTT GTA TGT ATG TAT GAT GACAGCCCCGGATGAGAAC-3' SEQ. ID. NO. 10
3. TOP-prim-19-Biot: 3'-AZA TZT AAA ZAT AZA TAZ ATA ZTA-CTGTCGGGGCCTACTCTTG-Biot-5' SEQ. ID. NO. 9
Top-F-Std43: 5'-TGT AGA TTT GTA TGT ATG TAT GAT GACAGCCCCGGATGAGAAC-3' SEQ. ID. NO. 19
HBE:
2. 3'-TTT CAT ATC ATT CTA CAT ATC ATC-CGGGGTCAACGGCAGATCCT-Biot-5' SEQ. ID. NO. 14
HBE-F-Std43: 5'-AAA GTA TAG TAA GAT GTA TAG TA GCCCCAGTTGCCGTCTAGGA-3' SEQ. ID. NO. 16
3. HBE-prim-20-Biot: 3'-TFT ZAT ATZ ATT ZTA ZAT ATZ AT-CGGGGTCAACGGCAGATCCT-Biot-5' SEQ. ID. NO. 15
HBE-F-Std43: 5'-AAA GTA TAG TAA GAT GTA TAG TA GCCCCAGTTGCCGTCTAGGA-3' SEQ. ID. NO. 16
MYC:
2. 3'-CAT AAA CTC ATT CAT TAA CTA ACT-AGGAGGAATACGGAGATAGTA-Biot-5' SEQ. ID. NO. 19
MYC-F-Std45: 5'-GTA TTT GAG TAA GTA ATT GAT TGA TCCTCCTTATGCCTCTATCAT-3' SEQ. ID. NO. 21
3. MYC-prim-21-Biot: 3'-ZAT AAA ZTZ ATT ZAT TAA ZTA AZT-AGGAGGAATACGGAGATAGTA-Biot-5' SEQ. ID. NO. 20
MYC-F-Std45: 5'-GTA TTT GAG TAA GTA ATT GAT TGA TCCTCCTTATGCCTCTATCAT-3' SEQ. ID. NO. 21
Procedure:
The same as in other Examples, but with these modifications.

Sample preparation:

| Components | GAP-2 Std-Biot/ Std-Temp | TOP-2 Std-Biot/ Std-Temp | HBE-2 Std-Biot/ Std-Temp | MYC-2 Std-Biot/ Std-Temp | 2-Mix Std-Biot/ Std-Temp | 3-Mix dZ-Biot/ Std-Temp | H₂O Negative |
|---|---|---|---|---|---|---|---|
| B-type beads mixture | 50 fmol/ 50 μL | 50 fmol/ 50 μL | 50 fmol/ 50 μL | 50 fmol/ 50 μL | 50 fmol/ 50 μL | 50 fmol/ 50 μL | 0 fmol/ 50 μL |

| Components | GAP-3 dZ-Biot/ Std-Temp | TOP-3 dZ-Biot/ Std-Temp | HBE-3 dZ-Biot/ Std-Temp | MYC-3 dZ-Biot/ Std-Temp | 3-Mix dZ-Biot/ Std-Temp | 2-Mix Std-Biot/ Std-Temp | H₂O Negative |
|---|---|---|---|---|---|---|---|
| C-type beads mixture | 50 fmol/ 50 μL | 50 fmol/ 50 μL | 50 fmol/ 50 μL | 50 fmol/ 50 μL | 50 fmol/ 50 μL | 50 fmol/ 50 μL | 0 fmol/ 50 μL |

Notes: 1. Four type of home-made bead (each has 5000 beads) in 50 μL of 2× Tm hybridization buffer were applied for each reaction.
2. B-type bead indicates Luminex COOH bead conjugate to standard oligonucleotide; C-type bead indicates that Luminex COOH bead conjugate to dP containing oligonucleotide.
3. The concentration of each biotin-labeled oligo is 10 fmoles/μL.
4. 2-Mix indicates that the mixture of GAP-2, TOP-2, HBE-2, and MYC-2 (the concentration of each oligo is 10 fmoles/μL); 3-Mix indicates that the mixture of GAP-3, TOP-3, HBE-3, and MYC-3 (the concentration of each oligo is 10 fmoles/μL).
5. After hybridization, 50 μL of 1×Tm hybridization buffer containing 6 μg/mL of streptavidin-R-phycoerythrin was added
to each reaction, and give 150 μL of final sample containing 2 μg/mL of streptavidin-R-phycoerythrin which was ready to be analyzed on Luminex machine.

Results. B-type beads mixture (3 + 10 + 14 + 19):

| Sample | Bead3 (GAP) | Bead10 (TOP) | Bead14 (HBE) | Bead19 (MYC) |
|---|---|---|---|---|
| B-MIX-GAP-2 | 6388 | 80 | 106 | 54 |
| B-MIX-TOP-2 | 92.5 | 938 | 90 | 66.5 |
| B-MIX-HBE-2 | 44 | 74 | 913.5 | 69 |
| B-MIX-MYC-2 | 74 | 51 | 84 | 1434 |
| B-MIX-2-MIX | 6283.5 | 884.5 | 1039.5 | 1457 |
| B-MIX-3-MIX | 2579 | 119 | 281 | 371 |
| B-MIX-H2O | 48 | 47 | 24 | 44 |

See FIG. 9 for results.

C-type beads mixture (3 + 10 + 14 + 19):

| Sample | Bead3 (GAP) | Bead10 (TOP) | Bead14 (HBE) | Bead19 (MYC) |
|---|---|---|---|---|
| C-MIX-GAP-3 | 4493.5 | 46 | 86 | 84 |
| C-MIX-TOP-3 | 69.5 | 4165 | 67 | 52 |
| C-MIX-HEB-3 | 26 | 56 | 3007 | 70 |
| C-MIX-MYC-3 | 70 | 19 | 36.5 | 3464 |
| C-MIX-3-MIX | 4418 | 4000 | 3093 | 3523 |
| C-MIX-2-MIX | 76.5 | 23 | 67.5 | 65 |
| C-MIX-H2O | 50 | 46.5 | 20 | 64 |

See FIG. 10 for results.

Example 3

Purpose

Luminex detection of the dZ containing oligo generated by primer extension.
Results:
1. The hybridization experiments demonstrate that the dP-containing oligonucleotides were successfully conjugated on to the Luminex carboxylated beads.
2. The Luminex beads with dP-containing oligo effectively distinguish between dZ-containing oligonucleotide from the standard oligonucleotide.
Oligonucleotides Used in this Study:
B. Positive control:
xTAG COOH Bead3(GAP-A), Bead10(TOP-A), Bead14(HBE-A), Bead19(MYC-A).
C. Coupling standard oligo to MicroPlex COOH Beads:
GAP-F-Lu3-NH2: 5'-NH$_2$—C$_{12}$-GAT TGT AAG ATT TGA TAA AGT GTA-3' (GAP-B) SEQ. ID. NO. 32
Top-F-Lu10-NH2: 5'-NH$_2$—C$_{12}$-TGT AGA TTT GTA TGT ATG TAT GAT-3' (TOP-B) SEQ. ID. NO. 25
HBE-F-Lu14-NH2: 5'-NH$_2$—C$_{12}$-AAA GTA TAG TAA GAT GTA TAG TAG-3' (HBE-B) SEQ. ID. NO. 26
MYC-F-Lu19-NH2: 5'-NH$_2$—C$_{12}$-GTA TTT GAG TAA GTA ATT GAT TGA-3' (MYC-B) SEQ. ID. NO. 27

D. Coupling dP containing oligo to MicroPlex COOH Beads:
GAP-F-Lu3-NH2-5P: 5'-NH$_2$—C$_{12}$-GAT TPT AAP ATT TPA TAA APT PTA-3' (GAP-C) SEQ. ID. NO. 28
Top-F-Lu10-NH2-5P: 5'-NH$_2$—C$_{12}$-TGT APA TTT PTA TPT ATP TAT PAT-3' (TOP-C) SEQ. ID. NO. 29
HBE-F-Lu14-NH2-5P: 5'-NH$_2$—C$_{12}$-AAA PTA TAP TAA PAT PTA TAP TAG-3' (HBE-C) SEQ. ID. NO. 30
MYC-F-Lu19-NH2-5P: 5'-NH$_2$—C$_{12}$-GTA TTT PAP TAA PTA ATT PAT TPA-3' (MYC-C) SEQ. ID. NO. 31
Complementary Biotin Labeled Oligonucleotides:
GAP:
1. Lua3-Std24-Biot: 3'-CTA ACA TTC TAA ACT ATT TCA CAT-Biot-5' SEQ. ID. NO. 7
2. 3'-CTA ACA TTC TAA ACT ATT TCA CAT-GGACTG-GACGGCAGATCTTTT-Biot-5' SEQ. ID. NO. 2
GAP-F-Std45: 5'-GAT TGT AAG ATT TGA TAA AGT GTA CCTGACCTGCCGTCTAGAAAA-3' SEQ. ID. NO. 4
3. GAP-prim-21-Biot: 3'-ZTA AZA TTZ TAA AZT ATT TZA ZAT-GGACTGGACGGCAGATCTTTT-Biot-5' SEQ. ID. NO. 3
GAP-F-Std45: 5'-GAT TGT AAG ATT TGA TAA AGT GTA CCTGACCTGCCGTCTAGAAAA-3' SEQ. ID. NO. 4
4. GAP-prim-21-Biot: 3'-CTA AZA TTZ TAA AZT ATT TZA ZAT-GGACTGGACGGCAGATCTTTT-Biot-5' SEQ. ID. NO. 5
GAP-F-45-5P: 5'-GAT TFT AAP ATT TPA TAA APT PTA CCTGACCTGCCGTCTAGAAAA-3' SEQ. ID. NO. 6
TOP:
1. Lua10-Std24-Biot: 3'-ACA TCT AAA CAT ACA TAC ATA CTA-Biot-5' SEQ. ID. NO. 7
2. 3'-ACA TCT AAA CAT ACA TAC ATA CTA-CTGTCGGGGCCTACTCTTG-Biot-5' SEQ. ID. NO. 8
Top-F-Std43: 5'-TGT AGA TTT GTA TGT ATG TAT GAT GACAGCCCCGGATGAGAAC-3' SEQ. ID. NO. 10
3. TOP-prim-19-Biot: 3'-AZA TZT AAA ZAT AZA TAZ ATA ZTA-CTGTCGGGGCCTACTCTTG-Biot-5' SEQ. ID. NO. 9
Top-F-Std43: 5'-TGT AGA TTT GTA TGT ATG TAT GAT GACAGCCCCGGATGAGAAC-3' SEQ. ID. NO. 10
4. TOP-prim-19-Biot: 3'-ACA TZT AAA ZAT AZA TAZ ATA ZTA-CTGTCGGGGCCTACTCTTG-Biot-5' SEQ. ID. NO. 11
Top-F-43-5P: 5'-TGT APA TTT PTA TPT ATP TAT PAT GACAGCCCCGGATGAGAAC-3' SEQ. ID. NO. 12
HBE:
1. Lua14-Std24-Biot: 3'-TTT CAT ATC ATT CIA CAT ATC ATC-Biot-5' SEQ. ID. NO. 13
2. 3'-TTT CAT ATC ATT CTA CAT ATC ATC-CGGGGTCAACGGCAGATCCT-Biot-5' SEQ. ID. NO. 14
HBE-F-Std43: 5'-AAA GTA TAG TAA GAT GTA TAG TA GCCCCAGTTGCCGTCTAGGA-3' SEQ. ID. NO. 16
3. HBE-prim-20-Biot: 3'-TTT ZAT ATZ ATT ZTA ZAT ATZ AT-CGGGGTCAACGGCAGATCCT-Biot-5' SEQ. ID. NO. 15
HBE-F-Std43: 5'-AAA GTA TAG TAA GAT GTA TAG TA GCCCCAGTTGCCGTCTAGGA-3' SEQ. ID. NO. 16
4. HBE-prim-20-Biot: 3'-TTT ZAT ATZ ATT ZTA ZAT ATZ AT-CGGGGTCAACGGCAGATCCT-Biot-5' SEQ. ID. NO. 15
HBE-F-43-5P: 5'-AAA PTA TAP TAA PAT PTA TAP TA GCCCCAGTTGCCGTCTAGGA-3' SEQ. ID. NO. 17
MYC:
1. Lua19-Std24-Biot: 3'-CAT AAA CTC ATT CAT TAA CTA ACT-Biot-5' SEQ. ID. NO. 18
2. 3'-CAT AAA CTC ATT CAT TAA CTA ACT-AGGAGGAATACGGAGATAGTA-Biot-5' SEQ. ID. NO. 19
MYC-F-Std45: 5'-GTA TTT GAG TAA GTA ATT GAT TGA TCCTCCTTATGCCTCTATCAT-3' SEQ. ID. NO. 21
3. MYC-prim-21-Biot: 3'-ZAT AAA ZTZ ATT ZAT TAA ZTA AZT-AGGAGGAATACGGAGATAGTA-Biot-5' SEQ. ID. NO. 20
MYC-F-Std45: 5'-GTA TTT GAG TAA GTA ATT GAT TGA TCCTCCTTATGCCTCTATCAT-3' SEQ. ID. NO. 21
4. MYC-prim-21-Biot: 3'-CAT AAA ZTZ ATT ZAT TAA ZTA AZT-AGGAGGAATACGGAGATAGTA-Biot-5' SEQ. ID. NO. 22
MYC-F-45-5P: 5'-GTA TTT PAP TAA PTA ATT PAT TPA TCCTCCTTATGCCTCTATCAT-3' SEQ. ID. NO. 23
Procedure:
Microspheres should be protected from prolonged exposure to light throughout this procedure.
1. Select the appropriate microsphere sets (A, B, and C) and resuspend by vortex and sonicated for approximately 20 seconds.
2. Combine 5000 microspheres of each set per reaction.
3. Concentrate the microsphere mixture by centrifugation at ≥8000×g for 1-2 minutes.
4. Remove the supernatant and resuspend to 100 of each microsphere set per µL in 2× Tm Hybridization Buffer by vortex and sonication for approximately 20 seconds. (Note: 50 µL are required for each reaction.)
5. Aliquot 50 µL of the microsphere mixture to each well.
6. Add 50 pt, of dH$_2$O to each background well.
7. Add 5 µL of biotinylated oligo (10 fmol/µL, complement to the oligo on the microsphere beads) to each sample wells.
8. Adjust the total volume to 100 µL by adding the appropriate volume of dH$^2$O to each sample well.
9. Cover the plate to prevent evaporation and denature at 95° C. for 120 seconds, then cool to 37° C. at a speed of 0.1° C./second (about 10 minutes).
10. Hybridize at 37° C. for another 10 minutes and then cool to room temperature.
11. Add 50 µL of 1× Tm Hybridization Buffer containing streptavidin-R-phycoerythrin to give 150 µL, of solution with 2 µg/mL of streptavidin-R-phycoerythrin (original concentration 2 µg/µL).
16. Incubate at 37° C. for 15 minutes, then store samples at 4° C. overnight.
17. The next day, the samples were warmed to room temperature and analyzed 45 µL at 25° C. on the Luminex analyzer according to the system manual.

| Sample preparation: | | | | | | | | |
|---|---|---|---|---|---|---|---|---|
| Components | GAP-B | GAP-C | TOP-B | TOP-C | HBE-B | HBE-C | MYC-B | MYC-C |
| 1. Std24-Biot | 50 fmol /50 µL | 50 fmol /50 µL | 50 fmol /50 µL | 50 fmol /50 µL | 50 fmol /50 µL | 50 fmol /50 µL | 50 fmol /50 µL | 50 fmol /50 µL |
| 2. Std-Biot/Std-Temp | 50 fmol /50 µL | 50 fmol /50 µL | 50 fmol /50 µL | 50 fmol /50 µL | 50 fmol /50 µL | 50 fmol /50 µL | 50 fmol /50 µL | 50 fmol /50 µL |

-continued

| Components | GAP-B | GAP-C | TOP-B | TOP-C | HBE-B | HBE-C | MYC-B | MYC-C |
|---|---|---|---|---|---|---|---|---|
| Sample preparation: | | | | | | | | |
| 3. dZ-Biot/Std-Temp | 50 fmol /50 µL | 50 fmol /50 µL | 50 fmol /50 µL | 50 fmol /50 µL | 50 fmol /50 µL | 50 fmol /50 µL | 50 fmol /50 µL | 50 fmol /50 µL |
| 4. dZ-Biot/dP-Temp | 50 fmol /50 µL | 50 fmol /50 µL | 50 fmol /50 µL | 50 fmol /50 µL | 50 fmol /50 µL | 50 fmol /50 µL | 50 fmol /50 µL | 50 fmol /50 µL |
| H$_2$O | 50 µL | 50 µL | 50 µL | 50 µL | 50 µL | 50 µL | 50 µL | 50 µL |

Notes: 1. 5000 beads in 50 µL of 2× Tm hybridization buffer were applied for each reaction.
2. B-type bead indicates Luminex COOH bead conjugate to standard oligonucleotide; C-type bead indicates that Luminex COOH bead conjugate to dP containing oligonucleotide.
3. A-type bead was bought from Luminex with standard oligo conjugated, which is positive control for B-type bead.
4. The concentration of each biotin-labeled oligo is 10 fmoles/µL.
5. After hybridization, 50 µL of 1× Tm hybridization buffer containing 6 µg/mL of streptavidin-R-phycoerythrin was added
to each reaction, and give 150 µL of final sample containing 2 µg/mL of streptavidin-R-phycoerythrin which was ready to be analyzed on Luminex machine.
Results:
  For results, see also FIGS. 10 and 11.

| GAP: | | | |
|---|---|---|---|
| Components | GAP-A | GAP-B | GAP-C |
| 1. Std24-Biot | 13246.5 | 15551 | 182 |
| 2. Std-Biot/Std-Temp | | 5844 | 13.5 |
| 3. dZ-Biot/Std-Temp | | 3080 | 4916 |
| 4. dZ-Biot/dP-Temp | | 2051 | 3194 |
| H$_2$O | | 71.5 | 64.5 |

| TOP: | | | |
|---|---|---|---|
| Components | TOP-A | TOP-B | TOP-C |
| 1. Std24-Biot | 16806 | 7057.5 | 182.5 |
| 2. Std-Biot/Std-Temp | | 1355.5 | 80 |
| 3. dZ-Biot/Std-Temp | | 82 | 4520.5 |
| 4. dZ-Biot/dP-Temp | | 173.5 | 2643.5 |
| H$_2$O | | 102 | 19 |

| HBE: | | | |
|---|---|---|---|
| Components | HBE-A | HBE-B | HBE-C |
| 1. Std24-Biot | 1995 | 16921 | 18 |
| 2. Std-Biot/Std-Temp | | 1713 | 120 |
| 3. dZ-Biot/Std-Temp | | 562.5 | 3392 |
| 4. dZ-Biot/dP-Temp | | 526 | 3058 |
| H$_2$O | | 33.5 | 57 |

| MYC: | | | |
|---|---|---|---|
| Components | MYC-A | MYC-B | MYC-C |
| 1. Std24-Biot | 14389.5 | 6047.5 | 283.5 |
| 2. Std-Biot/Std-Temp | | 1874 | 85 |
| 3. dZ-Biot/Std-Temp | | 636 | 4254.5 |
| 4. dZ-Biot/dP-Temp | | 337.5 | 2676 |
| H$_2$O | | 88.5 | 130 |

Example 4

Purpose

To compare the efficiency and fidelity of DNA polymerases (Taq, Vent (exo+), and DV (exo+)) to incorporate dZTP opposite two consecutive dPs in the template.
ThermoPol Reaction Buffer (20 mM Tris-HCl, 10 mM (NH$_4$)$_2$ SO$_4$, 10 mM KCl, 2 mM MgSO$_4$, 0.1% Triton X-100, pH=8.0).
Results:
  1. The order of the Fidelity of the polymerases tested is Deep Vent (exo+)>Vent (exo+)>Taq.
  2. In the absence of dZTP, Deep Vent and Vent just mis-incorporate one dCTP opposite the first dP. However, Taq can mis-incorporate dCTP opposite two consecutive dPs, then keep extending primer.
  3. The extension efficiency of Vent (exo+) seems better than DV (exo+) and Taq, this observation need to be tested using real-time PCR.
Oligonucletotides Used in this Study:

```
Negative control (-): dNTP (each 0.1 mM)
                                         SEQ. ID. NO. 33
T$_m$ = 59 T7-Y-RS-S16: 3'-GAAAT*CACTCCCAATTAAGCG-5'

T7-PP-Temp:
                                         SEQ. ID. NO. 34
5'-GCGTAATACGACTCACTATAGACGAPPCTACTTTAGTGAGGGTTAATT
CGC-3'

Positive control (+): dNTP (each 0.1 mM),
and dZTP (0.1 mM)
                                         SEQ. ID. NO. 33
T$_m$ = 59 T7-Y-RS-S16: 3'-GAAAT*CACTCCCAATTAAGCG-5'

T7-PP-Temp:
                                         SEQ. ID. NO. 34
5'-GCGTAATACGACTCACTATAGACGAPPCTACTTTAGTGAGGGTTAATT
CGC-3'
```

Procedure:
5'-$^{32}$P-labeled primer T7-Y-RS-S16 (0.2 pmole of hot primer plus 4 pmole of cold prime, final assay concentration 70 nM) was annealed to template T7-PP-Temp (6 pmole, final assay concentration 100 nM) in 1× Thermopol polymerase reaction buffer (pH=8.0 at room temperature) by heating (5 min at 95° C.) and then slow cooling (0.5 h) to room temperature. dNTP (each final 0.1 mM), and dZTP (final 0.1 mM, with (+) or without (−)) were added at room temperature. The reaction mixture was cooled to 4° C. for 1 min and followed by the addition of Taq (2.5 units), Vent (exo+), or Deep Vent (exo+) DNA polymerase (2 units for Vent and DV) to give a final volume of 60 μL. The primer was extended at 65° C. and aliquots (7) were taken from each reaction at time intervals (1, 2, 4, 8, and 16 min), quenched by PAGE loading/quench buffer (7 μL, 10 mM EDTA in formamide). Samples were resolved by electrophoresis using a 16% PAGE (7 M urea). The gel was analyzed using MolecularImager software.

Results:
See FIG. 12.

Example 5

Purpose

Compare the PCR efficiency of different template containing one dP, two dPs under the conditions of with dZ/PTPs or without dZ/PTPs.

Summary of the results (see also FIG. 13):
1. At pH=8.0, the PCR efficiency of dNTPs is better than that of dNTPs+dZ/PTPs;
2. In the absence of dZ/PTPs, there is significant amount of product generated from the dP containing template after 26 cycles of PCR amplification.
3. Using real-time PCR to monitor the PCR process.

Oligonucleotides Used in his Study:

T7-Z-RS-S16:
    SEQ. ID. NO. 35
5'-GCGTAATACGACTCACTATAG-3'
Tm = 57.2

T7-G-51-Std:
    SEQ. ID. NO. 36
5'-GCGTAATACGACTCACTATAGACGAGCGTACTTTAGTGAGGGTTAATT
CGC-3'

T7-P-Temp:
    SEQ. ID. NO. 37
5'-GCGTAATACGACTCACTATAGACGAPCGTACTTTAGTGAGGGTTAATT
CGC-5'

T7-PP-Temp:
    SEQ. ID. NO. 34
5'-GCGTAATACGACTCACTATAGACGAPPCTACTTTAGTGAGGGTTAATT
CGC-3'

Tm = 59 T7-Y-RS-S16:
    SEQ. ID. NO. 33
3'-GAAAT*CACTCCCAATTAAGCG-5'

| Components | Procedure: Volume (μl) | Final Concentration |
|---|---|---|
| Nuclease-Free Water (final volume of 40 μl) | 17 | |
| Forward Primer: T7-Z-RS-S16 (10 pmol/μl) | 1 | 0.25 μM |
| Reverse Primer: T7-Y-RS-S16 (10 pmol/μl) | 1 | 0.25 μM |
| Template: Three different Templates (A, B, and C) (0.01 pmol/μl) | 1 + 4 (H2O) | 0.25 nM |
| 10 × Thermopol Buffer (pH = 8.0) | 4 | |
| dNTP (2 mM) | 4 | 0.2 mM each |
| dZTP (2 mM) | 4 | 0.2 mM |
| dPTP (2 mM) | 4 | 0.2 mM |
| Hot Start Taq (5 U/μl) | 0.5 | 0.06 U/μl |

Note: 1× ThermoPol Reaction Buffer (20 mM Tris-HCl, 10 mM $(NH_4)_2SO_4$, 10 mM KCl, 2 mM $MgSO_4$, 0.1% Tritonx-100, pH 8.0 at 25° C.).

PCR conditions: one cycle of 95° C. for 15 min; 26 cycles of 95° C. for 20 s, (55° C. for 30 s, 72° C. for 1 min or 2 min; 72° C. for 5 min; 4° C. forever.

Results:

T7-G-51-Std:
    SEQ. ID. NO. 36
5'-GCGTAATACGACTCACTATAGACGAGCGTACTTTAGTGAGGGTTAATT
CGC-3'

(Template-A)
T7-P-Temp:
    SEQ. ID. NO. 37
5'-GCGTAATACGACTCACTATAGACGAPCGTACTTTAGTGAGGGTTAATT
CGC-5'

(Template-B)
T7-PP-Temp:
    SEQ. ID. NO. 34
5'-GCGTAATACGACTCACTATAGACGAPPCTACTTTAGTGAGGGTTAATT
CGC-3'

(Template-C)
    SEQ. ID. NO. 38
GTCGTTAAGACTTGTTCGGAGAGTA-5'
Tm = 65° C.

SEQ. ID. NO. 39
5'-CCGCAGTACAACCCAGGGGACAAAGATACCAAAATTGCCAAGAGGATG
GCTGTGTTGATCTTCACCGACTTCATATGCATGGCCCCAATCTCATTCTAT
GCTCTGTCAGCAATTCTGAACAAGCCTCCAT-3'

SEQ. ID. NO. 40
3'-GGCGTCATGTTGGGTCCCCTGTTTCTATGGTTTTAACGGTTCTCCTAC
CGACACAACTAGAAGTGGCTGAAGTATACGTACCGGGGTTAGAGTAAGATA
CGAGACAGTCGTTAAGACTTGTTCGGAGGTA-5'

SEQUENCE LISTING

<160> NUMBER OF SEQ ID NOS: 40

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1

```
tacactttat caaatcttac aatc                                            24
```

<210> SEQ ID NO 2
<211> LENGTH: 45
<212> TYPE: DNA
<213> ORGANISM: Artificial Sequence
<220> FEATURE:
<221> NAME/KEY: Misc_feature
<222> LOCATION: (24)..(24)
<223> OTHER INFORMATION: standard nucleotide
<220> FEATURE:
<223> OTHER INFORMATION: Synthetic

<400> SEQUENCE: 2

```
ttttctagac ggcaggtcag gtacacttta tcaaatctta caatc                     45
```

<210> SEQ ID NO 3
<211> LENGTH: 45
<212> TYPE: DNA
<213> ORGANISM: Artificial Sequence
<220> FEATURE:
<221> NAME/KEY: Misc_feature
<222> LOCATION: (24)..(24)
<223> OTHER INFORMATION: n= nonstandard nucleotide of the invention
<220> FEATURE:
<221> NAME/KEY: Misc_feature
<222> LOCATION: (26)..(26)
<223> OTHER INFORMATION: n = nonstandard nucleotide of the invention
<220> FEATURE:
<221> NAME/KEY: Misc_feature
<222> LOCATION: (32)..(32)
<223> OTHER INFORMATION: n= nonstandard nucleotide of the invention
<220> FEATURE:
<221> NAME/KEY: Misc_feature
<222> LOCATION: (37)..(37)
<223> OTHER INFORMATION: n= nonstandard nucleotide of the invention
<220> FEATURE:
<221> NAME/KEY: Misc_feature
<222> LOCATION: (41)..(41)
<223> OTHER INFORMATION: n= nonstandard nucleotide of the invention
<220> FEATURE:
<221> NAME/KEY: Misc_feature
<222> LOCATION: (45)..(45)
<223> OTHER INFORMATION: n= nonstandard nucleotide of the invention
<220> FEATURE:
<223> OTHER INFORMATION: Synthetic

<400> SEQUENCE: 3

```
ttttctagac ggcaggtcag gtananttta tnaaatntta naatn                     45
```

<210> SEQ ID NO 4
<211> LENGTH: 45
<212> TYPE: DNA
<213> ORGANISM: Artificial Sequence
<220> FEATURE:
<223> OTHER INFORMATION: Synthetic

<400> SEQUENCE: 4

```
gattgtaaga tttgataaag tgtacctgac ctgccgtcta gaaaa                     45
```

<210> SEQ ID NO 5
<211> LENGTH: 45
<212> TYPE: DNA
<213> ORGANISM: Artificial Sequence
<220> FEATURE:
<221> NAME/KEY: Misc_feature
<222> LOCATION: (24)..(24)
<223> OTHER INFORMATION: n= nonstandard nucleotide of the invention
<220> FEATURE:
<221> NAME/KEY: Misc_feature
<222> LOCATION: (26)..(26)

```
<223> OTHER INFORMATION: n= nonstandard nucleotide of the invention
<220> FEATURE:
<221> NAME/KEY: Misc_feature
<222> LOCATION: (32)..(32)
<223> OTHER INFORMATION: n= nonstandard nucleotide of the invention
<220> FEATURE:
<221> NAME/KEY: Misc_feature
<222> LOCATION: (37)..(37)
<223> OTHER INFORMATION: n= nonstandard nucleotide of the invention
<220> FEATURE:
<221> NAME/KEY: Misc_feature
<222> LOCATION: (41)..(41)
<223> OTHER INFORMATION: n= nonstandard nucleotide of the invention
<220> FEATURE:
<223> OTHER INFORMATION: Synthetic

<400> SEQUENCE: 5
ttttctagac ggcaggtcag gtananttta tnaaatntta naatc           45

<210> SEQ ID NO 6
<211> LENGTH: 45
<212> TYPE: DNA
<213> ORGANISM: Artificial Sequence
<220> FEATURE:
<221> NAME/KEY: Misc_feature
<222> LOCATION: (05)..(05)
<223> OTHER INFORMATION: n= nonstandard nucleotide of the invention
<220> FEATURE:
<221> NAME/KEY: Misc_feature
<222> LOCATION: (09)..(09)
<223> OTHER INFORMATION: n= nonstandard nucleotide of the invention
<220> FEATURE:
<221> NAME/KEY: Misc_feature
<222> LOCATION: (14)..(14)
<223> OTHER INFORMATION: n= nonstandard nucleotide of the invention
<220> FEATURE:
<221> NAME/KEY: Misc_feature
<222> LOCATION: (20)..(20)
<223> OTHER INFORMATION: n= nonstandard nucleotide of the invention
<220> FEATURE:
<221> NAME/KEY: Misc_feature
<222> LOCATION: (22)..(22)
<223> OTHER INFORMATION: n= nonstandard nucleotide of the invention
<220> FEATURE:
<223> OTHER INFORMATION: Synthetic

<400> SEQUENCE: 6
gattntaana tttnataaan tntacctgac ctgccgtcta gaaaa           45

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
atcatacata catacaaatc taca                                  24

<210> SEQ ID NO 8
<211> LENGTH: 43
<212> TYPE: DNA
<213> ORGANISM: Artificial Sequence
<220> FEATURE:
<223> OTHER INFORMATION: Synthetic

<400> SEQUENCE: 8
gttctcatcc ggggctgtca tcatacatac atacaaatct aca             43

<210> SEQ ID NO 9
<211> LENGTH: 43
```

```
<212> TYPE: DNA
<213> ORGANISM: Artificial Sequence
<220> FEATURE:
<221> NAME/KEY: Misc_feature
<222> LOCATION: (22)..(22)
<223> OTHER INFORMATION: n= nonstandard nucleotide of the invention
<220> FEATURE:
<221> NAME/KEY: Misc_feature
<222> LOCATION: (26)..(26)
<223> OTHER INFORMATION: n= nonstandard nucleotide of the invention
<220> FEATURE:
<221> NAME/KEY: Misc_feature
<222> LOCATION: (30)..(30)
<223> OTHER INFORMATION: n= nonstandard nucleotide of the invention
<220> FEATURE:
<221> NAME/KEY: Misc_feature
<222> LOCATION: (34)..(34)
<223> OTHER INFORMATION: n= nonstandard nucleotide of the invention
<220> FEATURE:
<221> NAME/KEY: Misc_feature
<222> LOCATION: (39)..(39)
<223> OTHER INFORMATION: n= nonstandard nucleotide of the invention
<220> FEATURE:
<221> NAME/KEY: Misc_feature
<222> LOCATION: (42)..(42)
<223> OTHER INFORMATION: n= nonstandard nucleotide of the invention
<220> FEATURE:
<223> OTHER INFORMATION: Synthetic

<400> SEQUENCE: 9
gttctcatcc ggggctgtca tnatanatan atanaaatnt ana                43

<210> SEQ ID NO 10
<211> LENGTH: 43
<212> TYPE: DNA
<213> ORGANISM: Artificial Sequence
<220> FEATURE:
<223> OTHER INFORMATION: Synthetic

<400> SEQUENCE: 10
tgtagatttg tatgtatgta tgatgacagc cccggatgag aac                43

<210> SEQ ID NO 11
<211> LENGTH: 43
<212> TYPE: DNA
<213> ORGANISM: Artificial Sequence
<220> FEATURE:
<221> NAME/KEY: Misc_feature
<222> LOCATION: (22)..(22)
<223> OTHER INFORMATION: n= nonstandard nucleotide of the invention
<220> FEATURE:
<221> NAME/KEY: Misc_feature
<222> LOCATION: (26)..(26)
<223> OTHER INFORMATION: n= nonstandard nucleotide of the invention
<220> FEATURE:
<221> NAME/KEY: Misc_feature
<222> LOCATION: (30)..(30)
<223> OTHER INFORMATION: n= nonstandard nucleotide of the invention
<220> FEATURE:
<221> NAME/KEY: Misc_feature
<222> LOCATION: (34)..(34)
<223> OTHER INFORMATION: n= nonstandard nucleotide of the invention
<220> FEATURE:
<221> NAME/KEY: Misc_feature
<222> LOCATION: (39)..(39)
<223> OTHER INFORMATION: n= nonstandard nucleotide of the invention
<220> FEATURE:
<223> OTHER INFORMATION: Synthetic

<400> SEQUENCE: 11
gttctcatcc ggggctgtca tnatanatan atanaaatnt aca                43

<210> SEQ ID NO 12
```

```
<211> LENGTH: 43
<212> TYPE: DNA
<213> ORGANISM: Artificial Sequence
<220> FEATURE:
<221> NAME/KEY: Misc_feature
<222> LOCATION: (05)..(05)
<223> OTHER INFORMATION: n= nonstandard nucleotide of the invention
<220> FEATURE:
<221> NAME/KEY: Misc_feature
<222> LOCATION: (10)..(10)
<223> OTHER INFORMATION: n= nonstandard nucleotide of the invention
<220> FEATURE:
<221> NAME/KEY: Misc_feature
<222> LOCATION: (14)..(14)
<223> OTHER INFORMATION: n= nonstandard nucleotide of the invention
<220> FEATURE:
<221> NAME/KEY: Misc_feature
<222> LOCATION: (18)..(18)
<223> OTHER INFORMATION: n= nonstandard nucleotide of the invention
<220> FEATURE:
<221> NAME/KEY: Misc_feature
<222> LOCATION: (22)..(22)
<223> OTHER INFORMATION: n= nonstandard nucleotide of the invention
<220> FEATURE:
<223> OTHER INFORMATION: Synthetic

<400> SEQUENCE: 12
tgtanatttn tatntatnta tnatgacagc cccggatgag aac            43

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
ctactataca tcttactata cttt                                 24

<210> SEQ ID NO 14
<211> LENGTH: 44
<212> TYPE: DNA
<213> ORGANISM: Artificial Sequence
<220> FEATURE:
<223> OTHER INFORMATION: Synthetic

<400> SEQUENCE: 14
tcctagacgg caactggggc ctactataca tcttactata cttt           44

<210> SEQ ID NO 15
<211> LENGTH: 43
<212> TYPE: DNA
<213> ORGANISM: Artificial Sequence
<220> FEATURE:
<221> NAME/KEY: Misc_feature
<222> LOCATION: (23)..(23)
<223> OTHER INFORMATION: n= nonstandard nucleotide of the invention
<220> FEATURE:
<221> NAME/KEY: Misc_feature
<222> LOCATION: (28)..(28)
<223> OTHER INFORMATION: n= nonstandard nucleotide of the invention
<220> FEATURE:
<221> NAME/KEY: Misc_feature
<222> LOCATION: (31)..(31)
<223> OTHER INFORMATION: n= nonstandard nucleotide of the invention
<220> FEATURE:
<221> NAME/KEY: Misc_feature
<222> LOCATION: (35)..(35)
<223> OTHER INFORMATION: n= nonstandard nucleotide of the invention
<220> FEATURE:
<221> NAME/KEY: Misc_feature
<222> LOCATION: (40)..(40)
<223> OTHER INFORMATION: n= nonstandard nucleotide of the invention
```

```
<220> FEATURE:
<223> OTHER INFORMATION: Synthetic

<400> SEQUENCE: 15
tcctagacgg caactggggc tantatanat nttantatan ttt                     43

<210> SEQ ID NO 16
<211> LENGTH: 43
<212> TYPE: DNA
<213> ORGANISM: Artificial Sequence
<220> FEATURE:
<223> OTHER INFORMATION: Synthetic

<400> SEQUENCE: 16
aaagtatagt aagatgtata gtagccccag ttgccgtcta gga                     43

<210> SEQ ID NO 17
<211> LENGTH: 43
<212> TYPE: DNA
<213> ORGANISM: Artificial Sequence
<220> FEATURE:
<221> NAME/KEY: Misc_feature
<222> LOCATION: (04)..(04)
<223> OTHER INFORMATION: n= nonstandard nucleotide of the invention
<220> FEATURE:
<221> NAME/KEY: Misc_feature
<222> LOCATION: (09)..(09)
<223> OTHER INFORMATION: n= nonstandard nucleotide of the invention
<220> FEATURE:
<221> NAME/KEY: Misc_feature
<222> LOCATION: (13)..(13)
<223> OTHER INFORMATION: n= nonstandard nucleotide of the invention
<220> FEATURE:
<221> NAME/KEY: Misc_feature
<222> LOCATION: (16)..(16)
<223> OTHER INFORMATION: n= nonstandard nucleotide of the invention
<220> FEATURE:
<221> NAME/KEY: Misc_feature
<222> LOCATION: (21)..(21)
<223> OTHER INFORMATION: n= nonstandard nucleotide of the invention
<220> FEATURE:
<223> OTHER INFORMATION: Synthetic

<400> SEQUENCE: 17
aaantatant aanatntata ntagccccag ttgccgtcta gga                     43

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
tcaatcaatt acttactcaa atac                                          24

<210> SEQ ID NO 19
<211> LENGTH: 45
<212> TYPE: DNA
<213> ORGANISM: Artificial Sequence
<220> FEATURE:
<223> OTHER INFORMATION: Synthetic

<400> SEQUENCE: 19
atgatagagg cataaggagg atcaatcaat tacttactca aatac                   45

<210> SEQ ID NO 20
<211> LENGTH: 45
<212> TYPE: DNA
```

```
<213> ORGANISM: Artificial Sequence
<220> FEATURE:
<221> NAME/KEY: Misc_feature
<222> LOCATION: (23)..(23)
<223> OTHER INFORMATION: n= nonstandard nucleotide of the invention
<220> FEATURE:
<221> NAME/KEY: Misc_feature
<222> LOCATION: (27)..(27)
<223> OTHER INFORMATION: n= nonstandard nucleotide of the invention
<220> FEATURE:
<221> NAME/KEY: Misc_feature
<222> LOCATION: (33)..(33)
<223> OTHER INFORMATION: n= nonstandard nucleotide of the invention
<220> FEATURE:
<221> NAME/KEY: Misc_feature
<222> LOCATION: (37)..(37)
<223> OTHER INFORMATION: n= nonstandard nucleotide of the invention
<220> FEATURE:
<221> NAME/KEY: Misc_feature
<222> LOCATION: (39)..(39)
<223> OTHER INFORMATION: n= nonstandard nucleotide of the invention
<220> FEATURE:
<221> NAME/KEY: Misc_feature
<222> LOCATION: (45)..(45)
<223> OTHER INFORMATION: n= nonstandard nucleotide of the invention
<220> FEATURE:
<223> OTHER INFORMATION: Synthetic

<400> SEQUENCE: 20
atgatagagg cataaggagg atnaatnaat tanttantna aatan              45

<210> SEQ ID NO 21
<211> LENGTH: 45
<212> TYPE: DNA
<213> ORGANISM: Artificial Sequence
<220> FEATURE:
<223> OTHER INFORMATION: Synthetic

<400> SEQUENCE: 21
gtatttgagt aagtaattga ttgatcctcc ttatgcctct atcat              45

<210> SEQ ID NO 22
<211> LENGTH: 45
<212> TYPE: DNA
<213> ORGANISM: Artificial Sequence
<220> FEATURE:
<221> NAME/KEY: Misc_feature
<222> LOCATION: (23)..(23)
<223> OTHER INFORMATION: n= nonstandard nucleotide of the invention
<220> FEATURE:
<221> NAME/KEY: Misc_feature
<222> LOCATION: (27)..(27)
<223> OTHER INFORMATION: n= nonstandard nucleotide of the invention
<220> FEATURE:
<221> NAME/KEY: Misc_feature
<222> LOCATION: (33)..(33)
<223> OTHER INFORMATION: n= nonstandard nucleotide of the invention
<220> FEATURE:
<221> NAME/KEY: Misc_feature
<222> LOCATION: (37)..(37)
<223> OTHER INFORMATION: n= nonstandard nucleotide of the invention
<220> FEATURE:
<221> NAME/KEY: Misc_feature
<222> LOCATION: (39)..(39)
<223> OTHER INFORMATION: n= nonstandard nucleotide of the invention
<220> FEATURE:
<223> OTHER INFORMATION: Synthetic

<400> SEQUENCE: 22
atgatagagg cataaggagg atnaatnaat tanttantna aatac              45

<210> SEQ ID NO 23
<211> LENGTH: 45
```

```
<212> TYPE: DNA
<213> ORGANISM: Artificial Sequence
<220> FEATURE:
<221> NAME/KEY: Misc_feature
<222> LOCATION: (7)..(7)
<223> OTHER INFORMATION: n= nonstandard nucleotide of the invention
<220> FEATURE:
<221> NAME/KEY: Misc_feature
<222> LOCATION: (9)..(9)
<223> OTHER INFORMATION: n= nonstandard nucleotide of the invention
<220> FEATURE:
<221> NAME/KEY: Misc_feature
<222> LOCATION: (13)..(13)
<223> OTHER INFORMATION: n= nonstandard nucleotide of the invention
<220> FEATURE:
<221> NAME/KEY: Misc_feature
<222> LOCATION: (19)..(19)
<223> OTHER INFORMATION: n= nonstandard nucleotide of the invention
<220> FEATURE:
<221> NAME/KEY: Misc_feature
<222> LOCATION: (23)..(23)
<223> OTHER INFORMATION: n= nonstandard nucleotide of the invention
<220> FEATURE:
<223> OTHER INFORMATION: Synthetic

<400> SEQUENCE: 23
gtatttnant aantaattna ttnatcctcc ttatgcctct atcat          45

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
gattgtaaga tttgataaag tgta                                 24

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
tgtagatttg tatgtatgta tgat                                 24

<210> SEQ ID NO 26
<211> LENGTH: 24
<212> TYPE: DNA
<213> ORGANISM: Artificial Sequence
<220> FEATURE:
<223> OTHER INFORMATION: Synthetic

<400> SEQUENCE: 26
aaagtatagt aagatgtata gtag                                 24

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
gtatttgagt aagtaattga ttga                                 24

<210> SEQ ID NO 28
```

```
<211> LENGTH: 24
<212> TYPE: DNA
<213> ORGANISM: Artificial Sequence
<220> FEATURE:
<221> NAME/KEY: Misc_feature
<222> LOCATION: (5)..(5)
<223> OTHER INFORMATION: n= nonstandard nucleotide of the invention
<220> FEATURE:
<221> NAME/KEY: Misc_feature
<222> LOCATION: (9)..(9)
<223> OTHER INFORMATION: n= nonstandard nucleotide of the invention
<220> FEATURE:
<221> NAME/KEY: Misc_feature
<222> LOCATION: (14)..(14)
<223> OTHER INFORMATION: n= nonstandard nucleotide of the invention
<220> FEATURE:
<221> NAME/KEY: Misc_feature
<222> LOCATION: (20)..(20)
<223> OTHER INFORMATION: n= nonstandard nucleotide of the invention
<220> FEATURE:
<221> NAME/KEY: Misc_feature
<222> LOCATION: (22)..(22)
<223> OTHER INFORMATION: n= nonstandard nucleotide of the invention
<220> FEATURE:
<223> OTHER INFORMATION: Synthetic

<400> SEQUENCE: 28
gattntaana tttnataaan tnta                                       24

<210> SEQ ID NO 29
<211> LENGTH: 24
<212> TYPE: DNA
<213> ORGANISM: Artificial Sequence
<220> FEATURE:
<221> NAME/KEY: Misc_feature
<222> LOCATION: (5)..(5)
<223> OTHER INFORMATION: n= nonstandard nucleotide of the invention
<220> FEATURE:
<221> NAME/KEY: Misc_feature
<222> LOCATION: (10)..(10)
<223> OTHER INFORMATION: n= nonstandard nucleotide of the invention
<220> FEATURE:
<221> NAME/KEY: Misc_feature
<222> LOCATION: (14)..(14)
<223> OTHER INFORMATION: n= nonstandard nucleotide of the invention
<220> FEATURE:
<221> NAME/KEY: Misc_feature
<222> LOCATION: (18)..(18)
<223> OTHER INFORMATION: n= nonstandard nucleotide of the invention
<220> FEATURE:
<221> NAME/KEY: Misc_feature
<222> LOCATION: (22)..(22)
<223> OTHER INFORMATION: n= nonstandard nucleotide of the invention
<220> FEATURE:
<223> OTHER INFORMATION: Synthetic

<400> SEQUENCE: 29
tgtanatttn tatntatnta tnat                                       24

<210> SEQ ID NO 30
<211> LENGTH: 24
<212> TYPE: DNA
<213> ORGANISM: Artificial Sequence
<220> FEATURE:
<221> NAME/KEY: Misc_feature
<222> LOCATION: (4)..(4)
<223> OTHER INFORMATION: n= nonstandard nucleotide of the invention
<220> FEATURE:
<221> NAME/KEY: Misc_feature
<222> LOCATION: (9)..(9)
<223> OTHER INFORMATION: n= nonstandard nucleotide of the invention
<220> FEATURE:
<221> NAME/KEY: Misc_feature
<222> LOCATION: (13)..(13)
<223> OTHER INFORMATION: n= nonstandard nucleotide of the invention
```

```
<220> FEATURE:
<221> NAME/KEY: Misc_feature
<222> LOCATION: (16)..(16)
<223> OTHER INFORMATION: n= nonstandard nucleotide of the invention
<220> FEATURE:
<221> NAME/KEY: Misc_feature
<222> LOCATION: (21)..(21)
<223> OTHER INFORMATION: n= nonstandard nucleotide of the invention
<220> FEATURE:
<223> OTHER INFORMATION: Synthetic

<400> SEQUENCE: 30
aaantatant aanatntata ntag                                              24

<210> SEQ ID NO 31
<211> LENGTH: 24
<212> TYPE: DNA
<213> ORGANISM: Artificial Sequence
<220> FEATURE:
<221> NAME/KEY: Misc_feature
<222> LOCATION: (7)..(7)
<223> OTHER INFORMATION: n= nonstandard nucleotide of the invention
<220> FEATURE:
<221> NAME/KEY: Misc_feature
<222> LOCATION: (9)..(9)
<223> OTHER INFORMATION: n= nonstandard nucleotide of the invention
<220> FEATURE:
<221> NAME/KEY: Misc_feature
<222> LOCATION: (13)..(13)
<223> OTHER INFORMATION: n= nonstandard nucleotide of the invention
<220> FEATURE:
<221> NAME/KEY: Misc_feature
<222> LOCATION: (19)..(19)
<223> OTHER INFORMATION: n= nonstandard nucleotide of the invention
<220> FEATURE:
<221> NAME/KEY: Misc_feature
<222> LOCATION: (23)..(23)
<223> OTHER INFORMATION: n= nonstandard nucleotide of the invention
<220> FEATURE:
<223> OTHER INFORMATION: Synthetic

<400> SEQUENCE: 31
gtatttnant aantaattna ttna                                              24

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
gattgtaaga tttgataaag tgta                                              24

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
gcgaattaac cctcactaaa g                                                 21

<210> SEQ ID NO 34
<211> LENGTH: 51
<212> TYPE: DNA
<213> ORGANISM: Artificial Sequence
<220> FEATURE:
<221> NAME/KEY: Misc_feature
<222> LOCATION: (26)..(26)
```

<223> OTHER INFORMATION: n= nonstandard nucleotide of the invention
<220> FEATURE:
<221> NAME/KEY: Misc_feature
<222> LOCATION: (27)..(27)
<223> OTHER INFORMATION: n= nonstandard nucleotide of the invention
<220> FEATURE:
<223> OTHER INFORMATION: Synthetic

<400> SEQUENCE: 34
gcgtaatacg actcactata gacganncta ctttagtgag ggttaattcg c    51

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
gcgtaatacg actcactata g    21

<210> SEQ ID NO 36
<211> LENGTH: 51
<212> TYPE: DNA
<213> ORGANISM: Artificial Sequence
<220> FEATURE:
<223> OTHER INFORMATION: Synthetic

<400> SEQUENCE: 36
gcgtaatacg actcactata gacgagcgta ctttagtgag ggttaattcg c    51

<210> SEQ ID NO 37
<211> LENGTH: 51
<212> TYPE: DNA
<213> ORGANISM: Artificial Sequence
<220> FEATURE:
<221> NAME/KEY: Misc_feature
<222> LOCATION: (26)..(26)
<223> OTHER INFORMATION: n= nonstandard nucleotide of the invention
<220> FEATURE:
<223> OTHER INFORMATION: Synthetic

<400> SEQUENCE: 37
gcgtaatacg actcactata gacgancgta ctttagtgag ggttaattcg c    51

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
atgagaggct tgttcagaat tgctg    25

<210> SEQ ID NO 39
<211> LENGTH: 130
<212> TYPE: DNA
<213> ORGANISM: Artificial Sequence
<220> FEATURE:
<223> OTHER INFORMATION: Synthetic

<400> SEQUENCE: 39
ccgcagtaca acccagggga caaagatacc aaaattgcca agaggatggc tgtgttgatc    60
ttcaccgact tcatatgcat ggccccaatc tcattctatg ctctgtcagc aattctgaac    120
aagcctccat    130

```
<210> SEQ ID NO 40
<211> LENGTH: 130
<212> TYPE: DNA
<213> ORGANISM: Artificial Sequence
<220> FEATURE:
<223> OTHER INFORMATION: Synthetic

<400> SEQUENCE: 40
atggaggctt gttcagaatt gctgacagag catagaatga gattgggcc atgcatatga      60 agtcggtgaa gatcaacaca gccatcctct tggcaatttt ggtatctttg tccoctgggt    120 tgtactgcgg                                                           130
```

What is claimed is:

1. A process for the addition of a nucleotide having, after incorporation, the structure

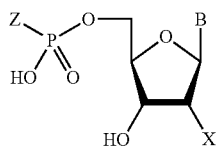

to the 3'-end of an oligonucleotide primer having a preselected sequence, wherein X is selected from the group consisting of —H and —OH, Z is the point of attachment to the 3'-end of said oligonucleotide primer, and B is selected from the group consisting of

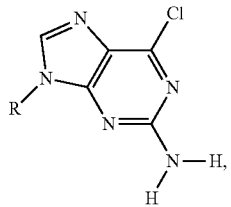 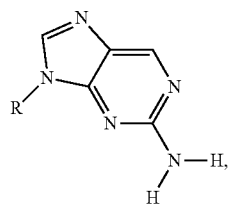

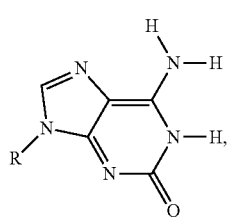 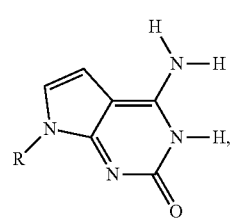

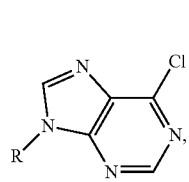 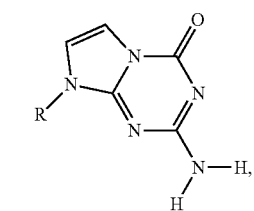

-continued

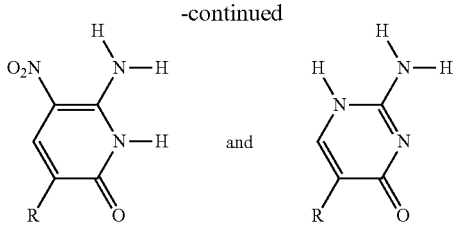 and 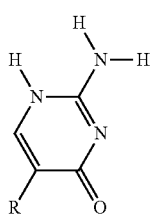

said process comprising contacting said primer in buffered aqueous solution with a template under conditions where said primer forms a duplex with said template, and incubating said duplex with a mixture of polymerase and polymerase substrates comprising the triphosphate

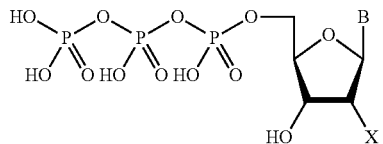

wherein X and B are defined as above, and wherein said added nucleotide is incorporated by said polymerase opposite a non-complementary standard nucleoside in the template selected from the group consisting of adenosine, guanosine, cytidine, uridine, and thymidine.

2. The process of claim 1 wherein B in both the added nucleotide and the nucleoside triphosphate is

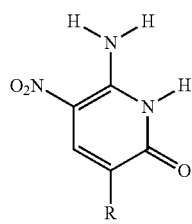

wherein R is the point of attachment of B to the nucleotide and nucleoside triphosphate, and wherein said opposite nucleoside in the template is the non-complementary guanosine.

3. The process of claim 1 wherein B in both the added nucleotide and the nucleoside triphosphate is

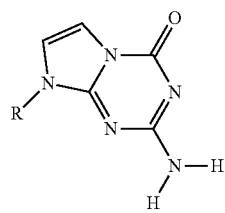

wherein R is the point of attachment of B to the nucleotide and the nucleoside triphosphate, and wherein said opposite nucleoside in the template is the non-complementary cytidine.

4. The process of claim 1 wherein B in both the added nucleotide and the nucleoside triphosphate is

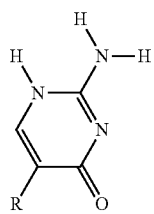

wherein R is the point of attachment of B to the nucleotide and the nucleoside triphosphate, and wherein said opposite nucleoside in the template is the non-complementary guanosine.

5. The process of claim 1 wherein B in both the added nucleotide and the nucleoside triphosphate is selected from the group consisting of

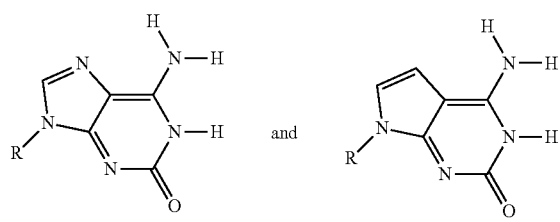

wherein R is the point of attachment of B to the nucleotide and the nucleoside triphosphate, and wherein said standard nucleoside in the template is selected from the group consisting of the non-complementary thymidine and uridine.

6. A process for the addition of a nucleoside selected from the group consisting of adenosine, guanosine, cytidine, uridine, and thymidine to the 3'-end of an oligonucleotide primer having a preselected sequence, said process comprising contacting said primer in buffered aqueous solution with a template under conditions where said primer forms a duplex with said template, and incubating said duplex with a mixture of polymerase and polymerase substrates comprising the triphosphate of adenosine, guanosine, cytidine, uridine, or thymidine, wherein said added nucleoside is incorporated opposite a nucleoside in the template having the structure

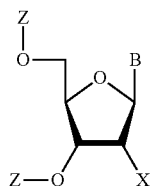

wherein X is selected from the group consisting of —H and —OH, Z is either hydrogen, phosphate, or the point of attachment to the 3'-end of said oligonucleotide template, and B is selected from the group consisting of

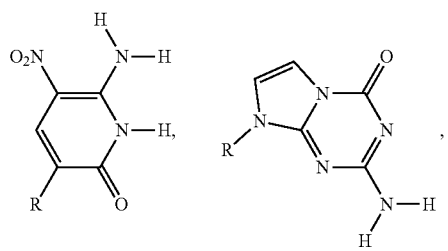

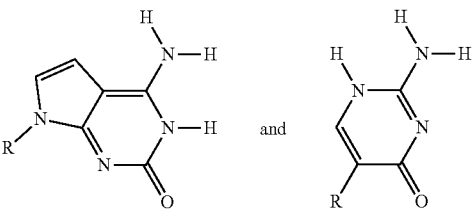

all of which are not complementary to adenosine, guanosine, cytidine, uridine, or thymidine.

7. The process of claim 6 wherein said added nucleoside is selected from the group consisting of uridine and thymidine, said triphosphate is selected from the group consisting of thymidine triphosphate and uridine triphosphate, and said B in the template is the non-complementary

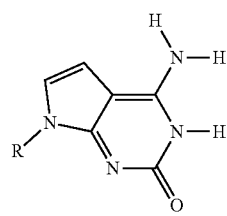

wherein R is the point of attachment of B to the template.

8. The process of claim 6 wherein said added nucleoside is guanosine, and said B in the template is the non-complementary

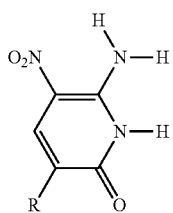

wherein R is the point of attachment of B to the template.

9. The process of claim 6 wherein said added nucleoside is cytidine, and said B in the template is the non-complementary

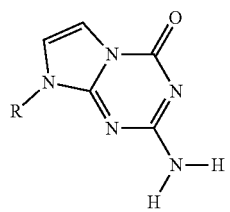

wherein R is the point of attachment of B to the template.

10. The process of claim 6 wherein said added nucleoside is guanosine, and said B in the template is the non-complementary

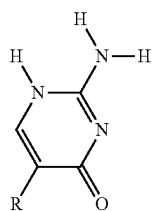

wherein R is the point of attachment of B to the template.

11. A process for the addition of a nucleotide having, after incorporation, the structure

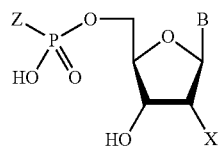

to the 3'-end of an oligonucleotide primer having a preselected sequence, wherein X is selected from the group consisting of —H and —OH, Z is the point of attachment to the 3'-end of said oligonucleotide primer, and B is selected from the group consisting of

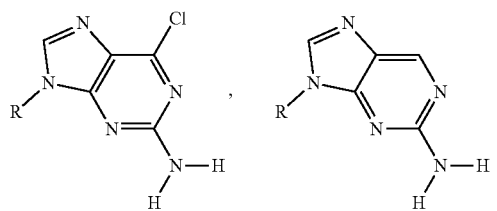

and

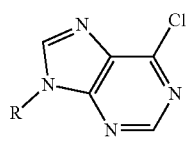

said process comprising contacting said primer in buffered aqueous solution with a template under conditions where said primer forms a duplex with said template, and incubating said duplex with a mixture of polymerase and polymerase substrates comprising the triphosphate

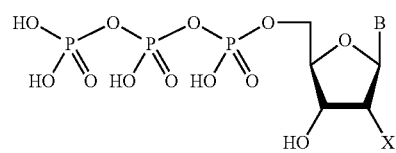

wherein said added nucleotide is incorporated opposite a nucleoside in the template having the

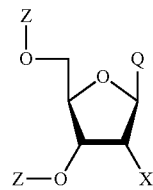

wherein X is selected from the group consisting of —H and —OH, Z is either hydrogen, phosphate, or the point of attachment to the 3'-end of said oligonucleotide template, and Q is

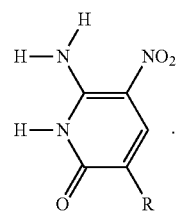

12. A process for the addition of a nucleotide having, after incorporation, the structure

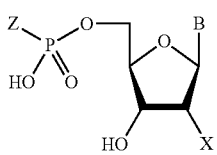

to the 3'-end of an oligonucleotide primer having a preselected sequence, wherein X is selected from the group consisting of —H and —OH, Z is the point of attachment to the 3'-end of said oligonucleotide primer, and B is selected from the group consisting of

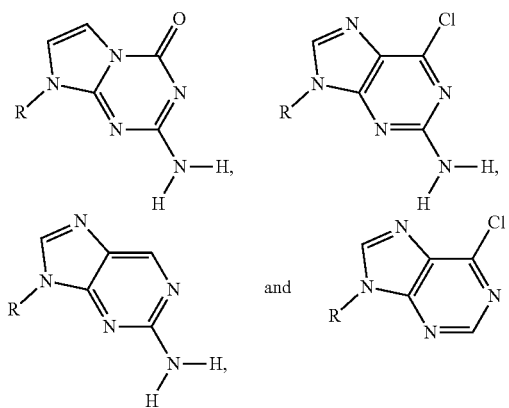

said process comprising contacting said primer in buffered aqueous solution with a template under conditions where said primer forms a duplex with said template, and incubating said duplex with a polymerase and polymerase substrates comprising the triphosphate

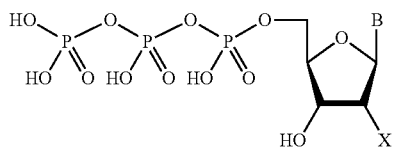

wherein B and X are defined as before, wherein said added nucleotide is incorporated opposite a nucleoside in the template having the structure

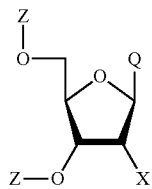

wherein X is selected from the group consisting of —H and —OH, Z is either hydrogen, phosphate, or the point of attachment to the 3'-end of said oligonucleotide template, and Q is selected from the group consisting of

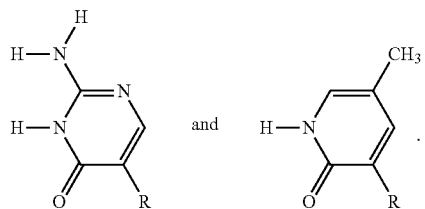

* * * * *